United States Patent
Sakamoto et al.

(10) Patent No.: US 9,512,251 B2
(45) Date of Patent: Dec. 6, 2016

(54) POLYMERIZABLE COMPOUND, POLYMERIZABLE COMPOSITION, POLYMER, AND OPTICALLY ANISOTROPIC MATERIAL

(71) Applicant: ZEON CORPORATION, Tokyo (JP)

(72) Inventors: Kei Sakamoto, Tokyo (JP); Kumi Okuyama, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 87 days.

(21) Appl. No.: 14/404,723

(22) PCT Filed: May 30, 2013

(86) PCT No.: PCT/JP2013/065039
§ 371 (c)(1),
(2) Date: Dec. 1, 2014

(87) PCT Pub. No.: WO2013/180217
PCT Pub. Date: Dec. 5, 2013

(65) Prior Publication Data
US 2015/0183902 A1 Jul. 2, 2015

(30) Foreign Application Priority Data

May 30, 2012 (JP) .................. 2012-123422
Jul. 6, 2012 (JP) .................. 2012-153058
Oct. 19, 2012 (JP) .................. 2012-232315

(51) Int. Cl.
*C08F 122/24* (2006.01)
*G02B 1/08* (2006.01)
*C08F 222/24* (2006.01)
*C07D 513/04* (2006.01)
*C07D 277/82* (2006.01)
(Continued)

(52) U.S. Cl.
CPC ........... *C08F 122/24* (2013.01); *C07D 277/82* (2013.01); *C07D 513/04* (2013.01); *C08F 222/24* (2013.01); *C09K 19/24* (2013.01); *C09K 19/322* (2013.01); *C09K 19/348* (2013.01); *C09K 19/3486* (2013.01); *C09K 19/3488* (2013.01); *C09K 19/3497* (2013.01); *C09K 19/3852* (2013.01); *G02B 1/08* (2013.01); *G02B 5/3025* (2013.01); *C08F 2222/102* (2013.01); *C09K 2019/0448* (2013.01); *C09K 2019/2078* (2013.01)

(58) Field of Classification Search
CPC .... C07D 277/82; C07D 513/04; C08F 122/24; C08F 222/24; C08F 2222/102; C09K 19/24; C09K 19/322; C09K 19/348; C09K 19/3486; C09K 19/3488; C09K 19/3497; C09K 19/3852; C09K 2019/0448; C09K 2019/2078; G02B 1/08; G02B 5/3025

USPC ........... 526/257; 544/350; 546/114; 548/126, 548/161
See application file for complete search history.

(56) References Cited

U.S. PATENT DOCUMENTS 5,567,349 A * 10/1996 Kelly ................. C07C 69/92
                                                     252/299.01
5,863,457 A    1/1999 Hasebe et al.
(Continued)

FOREIGN PATENT DOCUMENTS

EP    2 871 192 A1    5/2015
JP    10-68816 A      3/1998
(Continued)

OTHER PUBLICATIONS

Jul. 16, 2013 International Search Report issued in Patent Application No. PCT/JP2013/065039.
(Continued)

*Primary Examiner* — Ling Choi
*Assistant Examiner* — Chun-Cheng Wang
(74) *Attorney, Agent, or Firm* — Oliff PLC

(57) ABSTRACT

The present invention relates to: a polymerizable compound (I), wherein $Y^1$ to $Y^6$ are a chemical single bond, —O—C(=O)—, —C(=O)—O— or the like, $G^1$ and $G^2$ are a divalent aliphatic group, $Z^1$ and $Z^2$ are an alkenyl group, $A^x$ is a fused ring group represented by a formula (II), wherein X is —NR$^3$—, an oxygen atom, a sulfur atom or the like, $R^3$ is a hydrogen atom or an alkyl group having 1 to 6 carbon atoms, and D is a substituted or unsubstituted ring having 1 to 20 carbon atoms that includes at least one nitrogen atom, $A^y$ is a hydrogen atom, an alkyl group, $A^1$ is a trivalent aromatic group or the like, $A^2$ and $A^3$ are a divalent aromatic group having 6 to 30 carbon atoms or the like, and $Q^1$ is a hydrogen atom, or an alkyl group having 1 to 6 carbon atoms.

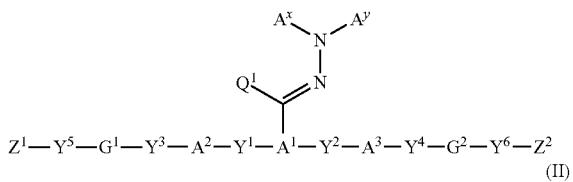

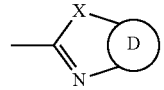

13 Claims, No Drawings

(51) Int. Cl.
*C09K 19/24* (2006.01)
*C09K 19/32* (2006.01)
*C09K 19/34* (2006.01)
*C09K 19/38* (2006.01)
*G02B 5/30* (2006.01)
*C09K 19/04* (2006.01)
*C09K 19/20* (2006.01)
*C08F 222/10* (2006.01)

(56) References Cited

U.S. PATENT DOCUMENTS

| | | | |
|---|---|---|---|
| 6,139,771 | A | 10/2000 | Walba et al. |
| 6,203,724 | B1 | 3/2001 | Reiffenrath et al. |
| 6,565,974 | B1 | 5/2003 | Uchiyama et al. |
| 2002/0159005 | A1 | 10/2002 | Arakawa et al. |
| 2003/0102458 | A1 | 6/2003 | Nishikawa et al. |
| 2007/0176145 | A1 | 8/2007 | Nishikawa et al. |
| 2007/0298191 | A1 | 12/2007 | Yamahara et al. |
| 2009/0072194 | A1 | 3/2009 | Yamahara et al. |
| 2009/0189120 | A1 | 7/2009 | Takeuchi |
| 2010/0201920 | A1 | 8/2010 | Adlem et al. |
| 2010/0258764 | A1 | 10/2010 | Sakamoto et al. |
| 2010/0301271 | A1 | 12/2010 | Adlem et al. |
| 2011/0237768 | A1 | 9/2011 | Katoh et al. |
| 2014/0107247 | A1 | 4/2014 | Sakamoto et al. |
| 2014/0142266 | A1 | 5/2014 | Sakamoto et al. |
| 2014/0309396 | A1 | 10/2014 | Sakamoto et al. |

FOREIGN PATENT DOCUMENTS

| | | |
|---|---|---|
| JP | 10-90521 A | 4/1998 |
| JP | 11-52131 A | 2/1999 |
| JP | 2001-004837 A | 1/2001 |
| JP | 2001-234154 A | 8/2001 |
| JP | 2002-267838 A | 9/2002 |
| JP | 2005-208414 A | 8/2005 |
| JP | 2005-208415 A | 8/2005 |
| JP | 2005-208416 A | 8/2005 |
| JP | 2010-001284 A | 1/2010 |
| JP | 2010-031223 A | 2/2010 |
| JP | 2010-070505 A | 4/2010 |
| JP | 2011-006360 A | 1/2011 |
| JP | 2011-006361 A | 1/2011 |
| JP | 2011-042606 A | 3/2011 |
| WO | 00/26705 A1 | 5/2000 |
| WO | 2012141245 A1 | 10/2012 |
| WO | 2012147904 A1 | 11/2012 |
| WO | 2012176679 A1 | 12/2012 |

OTHER PUBLICATIONS

Dec. 22, 2015 Extended Search Report issued in European Patent Application No. 13796461.5.

* cited by examiner

POLYMERIZABLE COMPOUND, POLYMERIZABLE COMPOSITION, POLYMER, AND OPTICALLY ANISOTROPIC MATERIAL

TECHNICAL FIELD

The invention relates to a polymerizable compound, a polymerizable composition, and a polymer that may produce an optical film that achieves uniform conversion of polarized light over a wide wavelength band, and also relates to an optically anisotropic article.

BACKGROUND ART

A flat panel display (FPD) that utilizes an optical film (e.g., polarizer and retardation film) can achieve high-resolution display, and has been widely used as a display device (e.g., TV) that exhibits high performance.

Examples of the retardation film include a quarter-wave plate that converts linearly polarized light into circularly polarized light, and a half-wave plate that converts the plane of vibration of linearly polarized light by 90°. Such a retardation film can achieve accurate conversion of specific monochromatic light so that ¼λ or ½λ retardation occurs.

However, a known retardation film has a problem in that polarized light that passes through the retardation film is converted into colored polarized light. Specifically, since a material that forms the retardation film has wavelength dispersion with regard to retardation, and a polarization state distribution corresponding to each wavelength occurs for white light that includes different light beams in the visible region, it is impossible to achieve accurate ¼λ or ½λ retardation over the entire wavelength band.

In order to solve the above problem, various wideband retardation films that can achieve uniform retardation for light over a wide wavelength band (i.e., retardation films having reverse wavelength dispersion) have been studied (see Patent Documents 1 to 6, for example).

It has been desired to reduce the thickness of the flat panel display as much as possible along with an improvement in performance and widespread use of mobile information terminals (e.g., mobile personal computer and mobile phone). Therefore, a reduction in thickness of the retardation film has also been desired.

It has been considered that it is most effective to produce a retardation film by applying a polymerizable composition that includes a low-molecular-weight polymerizable compound to a film substrate in order to reduce the thickness of the retardation film. Various low-molecular-weight polymerizable compounds having excellent wavelength dispersion, and various polymerizable compositions using such polymerizable compounds have been developed (see Patent Documents 7 to 24, for example).

However, the low-molecular-weight polymerizable compounds or the polymerizable compositions disclosed in Patent Documents 7 to 24 have a number of problems in that reverse wavelength dispersion may be insufficient, or it may be difficult to apply the low-molecular-weight polymerizable compounds or the polymerizable compositions to a film due to a high melting point that is not suitable for an industrial process, or the temperature range in which liquid crystallinity is obtained may be very narrow, or solubility in a solvent generally used for an industrial process may be low. Moreover, since the above low-molecular-weight polymerizable compounds and the like are synthesized in a plurality of steps using a synthesis method that utilizes an expensive reagent, the production cost increases.

RELATED-ART DOCUMENT

Patent Document

Patent Document 1: JP-A-10-68816
Patent Document 2: JP-A-10-90521
Patent Document 3: JP-A-11-52131
Patent Document 4: JP-A-2000-284126 (US20020159005A1)
Patent Document 5: JP-A-2001-4837
Patent Document 6: WO2000/026705
Patent Document 7: JP-A-2002-267838
Patent Document 8: JP-A-2003-160540 (US20030102458A1)
Patent Document 9: JP-A-2005-208414
Patent Document 10: JP-A-2005-208415
Patent Document 11: JP-A-2005-208416
Patent Document 12: JP-A-2005-289980 (US20070176145A1)
Patent Document 13: JP-A-2006-330710 (US20090072194A1)
Patent Document 14: JP-A-2009-179563 (US20090189120A1)
Patent Document 15: JP-A-2010-31223
Patent Document 16: JP-A-2011-6360
Patent Document 17: JP-A-2011-6361
Patent Document 18: JP-A-2011-42606
Patent Document 19: JP-T-2010-537954 (US20100201920A1)
Patent Document 20: JP-T-2010-537955 (US20100301271A1)
Patent Document 21: WO2006/052001 (US20070298191A1)
Patent Document 22: U.S. Pat. No. 6,139,771
Patent Document 23: U.S. Pat. No. 6,203,724
Patent Document 24: U.S. Pat. No. 5,567,349

SUMMARY OF THE INVENTION

Technical Problem

The invention was conceived in view of the above situation. An object of the invention is to provide a polymerizable compound, a polymerizable composition, and a polymer that have a practical low melting point, exhibit excellent solubility in a general-purpose solvent, can be produced at low cost, and can produce an optical film that achieves uniform conversion of polarized light over a wide wavelength band, and an optically anisotropic article.

Solution to Problem

The inventors of the invention conducted extensive studies in order to achieve the above object. As a result, the inventors found that an optical film that achieves uniform conversion of polarized light over a wide wavelength band, and exhibits satisfactory performance, can be produced at low cost by utilizing an optically anisotropic article produced using a polymer that is obtained by polymerizing a polymerizable compound represented by the following formula (I), or a polymerizable composition that includes the polymerizable compound and an initiator. This finding has led to the completion of the invention.

Several aspects of the invention provide the following polymerizable compound (see (1) to (7)), polymerizable composition (see (8) and (9)), polymer (see (10) and (11)), and optically anisotropic article (see (12)).

(1) A polymerizable compound represented by the following formula (I),

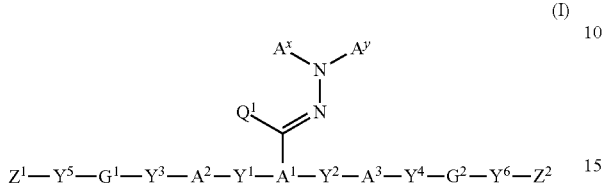

wherein $Y^1$ to $Y^6$ are independently a chemical single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$—, or —NR$^1$—O—,
$R^1$ is a hydrogen atom or an alkyl group having 1 to 6 carbon atoms,
$G^1$ and $G^2$ are independently a substituted or unsubstituted divalent aliphatic group having 1 to 20 carbon atoms that optionally includes —O—, —S—, —O—C(=O)—, —C(=O)—O—, —O—C(=O)—O—, —NR$^2$—C(=O)—, —C(=O)—NR$^2$—, —NR$^2$—, or —C(=O)—, provided that a case where the aliphatic group includes two or more adjacent —O— or —S— is excluded, $R^2$ is a hydrogen atom or an alkyl group having 1 to 6 carbon atoms,
$Z^1$ and $Z^2$ are independently an alkenyl group having 2 to 10 carbon atoms that is unsubstituted, or substituted with a halogen atom,
$A^x$ is a fused ring group represented by the following formula (II),

wherein X is —NR$^3$—, an oxygen atom, a sulfur atom, —C(=O)—, —SO—, or —SO$_2$—, $R^3$ is a hydrogen atom or an alkyl group having 1 to 6 carbon atoms, and D is a substituted or unsubstituted ring having 1 to 20 carbon atoms that includes at least one nitrogen atom, $A^y$ is a hydrogen atom, a substituted or unsubstituted alkyl group having 1 to 20 carbon atoms, a substituted or unsubstituted alkenyl group having 2 to 20 carbon atoms, a substituted or unsubstituted cycloalkyl group having 3 to 18 carbon atoms, —C(=O)—R$^4$, —SO$_2$—R$^5$, or an organic group having 2 to 30 carbon atoms that includes at least one aromatic ring selected from the group consisting of an aromatic hydrocarbon ring and an aromatic heterocyclic ring, provided that the aromatic ring is either substituted or unsubstituted, $R^4$ is a substituted or unsubstituted alkyl group having 1 to 20 carbon atoms, a substituted or unsubstituted alkenyl group having 2 to 20 carbon atoms, or a substituted or unsubstituted cycloalkyl group having 3 to 18 carbon atoms, $R^5$ is an alkyl group having 1 to 20 carbon atoms, an alkenyl group having 2 to 20 carbon atoms, a phenyl group, or a 4-methylphenyl group,
$A^1$ is a substituted or unsubstituted trivalent aromatic group, $A^2$ and $A^3$ are independently a substituted or unsubstituted divalent aromatic group having 6 to 30 carbon atoms, and $Q^1$ is a hydrogen atom, or a substituted or unsubstituted alkyl group having 1 to 6 carbon atoms.

(2) The polymerizable compound according to (1), wherein $A^x$ is a fused ring group represented by the following formula (II-1), a fused ring group represented by the following formula (II-2), a fused ring group represented by the following formula (II-3), a fused ring group represented by the following formula (II-4), or a fused ring group represented by the following formula (II-5),

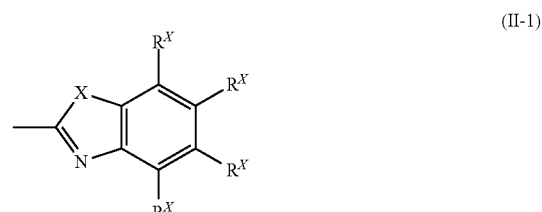

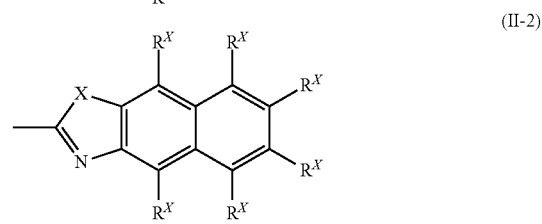

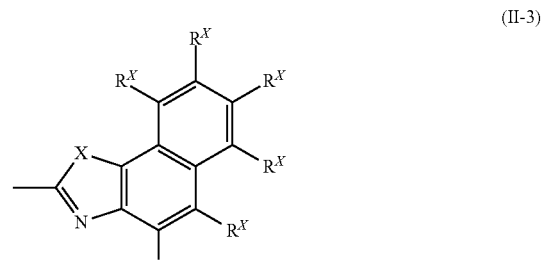

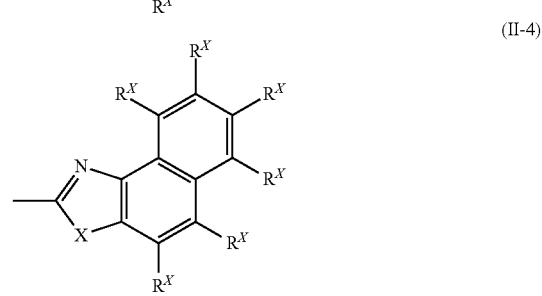

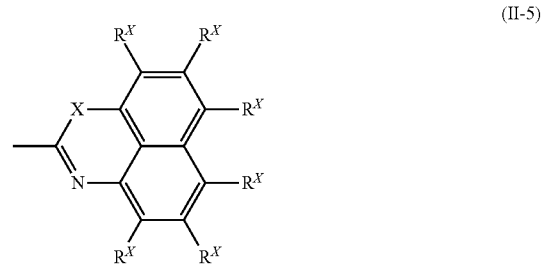

wherein X is the same as defined above, at least one C—R$^X$ in each formula is substituted with a nitrogen atom, R$^X$ are a hydrogen atom, a halogen atom, an alkyl group having 1 to 6 carbon atoms, a cyano group, a nitro group, an alkylsulfinyl group having 1 to 6 carbon atoms, an alkylsulfonyl group having 1 to 6 carbon atoms, a fluoroalkyl group having 1 to 6 carbon atoms, an alkoxy group having 1 to 6 carbon atoms, an alkylthio group having 1 to 6 carbon atoms, a monosubstituted amino group, a disubstituted amino group, an alkylsulfamoyl group having 1 to 6 carbon atoms, a dialkylsulfamoyl group having 2 to 12 carbon atoms, or —C(=O)—O—$R^6$, and $R^6$ is a hydrogen atom or an alkyl group having 1 to 6 carbon atoms, provided that $R^x$ are either identical or different.

(3) The polymerizable compound according to (1) or (2), wherein $A^1$ is a substituted or unsubstituted trivalent benzene ring group, or a substituted or unsubstituted trivalent naphthalene ring group, and $A^2$ and $A^3$ are independently a substituted or unsubstituted phenylene group, or a substituted or unsubstituted naphthylene group.

(4) The polymerizable compound according to any one of (1) to (3), wherein $Y^1$ to $Y^6$ are independently a chemical single bond, —O—, —O—C(=O)—, —C(=O)—O—, or —O—C(=O)—O—.

(5) The polymerizable compound according to any one of (1) to (4), wherein $Z^1$ and $Z^2$ are independently $CH_2$=CH—, $CH_2$=C($CH_3$)—, or $CH_2$=C(Cl)—.

(6) The polymerizable compound according to any one of (1) to (5), wherein $G^1$ and $G^2$ are independently a substituted or unsubstituted divalent aliphatic group having 1 to 12 carbon atoms that optionally includes —O—, —O—C(=O)—, —C(=O)—O—, or —C(=O)—, provided that a case where the aliphatic group includes two or more adjacent —O— is excluded.

(7) The polymerizable compound according to any one of (1) to (5), wherein $G^1$ and $G^2$ are independently a divalent alkylene group having 1 to 12 carbon atoms.

(8) A polymerizable composition including at least one type of the polymerizable compound according to any one of (1) to (7).

(9) A polymerizable composition including the polymerizable compound according to any one of (1) to (7), and an initiator.

(10) A polymer obtained by polymerizing the polymerizable compound according to any one of (1) to (7), or the polymerizable composition according to (8) or (9).

(11) The polymer according to (10), the polymer being a liquid crystalline polymer.

(12) An optically anisotropic article including the polymer according to (11).

Advantageous Effects of the Invention

The polymerizable compound, the polymerizable composition, and the polymer according to the aspects of the invention make it possible to inexpensively obtain an optically anisotropic article that achieves uniform conversion of polarized light over a wide wavelength band, and exhibits satisfactory performance.

Since the optically anisotropic article according to the aspect of the invention is produced using the polymer according to the aspect of the invention, the optically anisotropic article can be produced at low cost, achieves uniform conversion of polarized light over a wide wavelength band, and exhibits satisfactory performance.

For example, an antireflective film may be produced by combining the film-shaped optically anisotropic article according to the aspect of the invention with a polarizer. The antireflective film may suitably be used to prevent reflection from a touch panel, an organic electroluminescent device, and the like.

DESCRIPTION OF EMBODIMENTS

A polymerizable compound, a polymerizable composition, a polymer, and an optically anisotropic article according to several exemplary embodiments of the invention are described in detail below. Note that the expression "substituted or unsubstituted" used herein in connection with a group or the like means that the group or the like is unsubstituted, or substituted with a substituent.

1) Polymerizable Compound

A polymerizable compound according to one embodiment of the invention is a compound represented by the formula (I).

$Y^1$ to $Y^6$ in the formula (I) are independently a chemical single bond, —O—, —S—, —O—C(=O)—, —C(=O)—O—, —O—C(=O)—O—, —$NR^1$—C(=O)—, —C(=O)—$NR^1$—, —O—C(=O)—$NR^1$—, —$NR^1$—C(=O)—O—, —$NR^1$—C(=O)—$NR^1$—, —O—$NR^1$—, or —$NR^1$—O—.

$R^1$ is a hydrogen atom or an alkyl group having 1 to 6 carbon atoms.

Examples of the alkyl group having 1 to 6 carbon atoms represented by $R^1$ include a methyl group, an ethyl group, an n-propyl group, an isopropyl group, an n-butyl group, a sec-butyl group, a t-butyl group, an n-pentyl group, an n-hexyl group, and the like.

$R^1$ is preferably a hydrogen atom or an alkyl group having 1 to 4 carbon atoms.

It is preferable that $Y^1$ to $Y^6$ be independently a chemical single bond, —O—, —O—C(=O)—, —C(=O)—O—, or —O—C(=O)—O—.

$G^1$ and $G^2$ are independently a substituted or unsubstituted divalent aliphatic group having 1 to 20 carbon atoms.

Examples of the divalent aliphatic group having 1 to 20 carbon atoms include divalent aliphatic groups having a linear structure, such as an alkylene group having 1 to 20 carbon atoms, an alkenylene group having 1 to 20 carbon atoms, and an alkynylene group having 1 to 20 carbon atoms; divalent aliphatic groups having an alicyclic structure, such as a cycloalkanediyl group having 3 to 20 carbon atoms, an alkenediyl group having 4 to 20 carbon atoms, and a divalent fused alicyclic group having 10 to 20 carbon atoms; and the like.

Examples of a substituent that may substitute the divalent aliphatic group having a linear structure represented by $G^1$ and $G^2$ include halogen atoms such as a fluorine atom, a chlorine atom, a bromine atom, and an iodine atom; alkoxy groups having 1 to 6 carbon atoms, such as a methoxy group, an ethoxy group, an n-propoxy group, an isopropoxy group, an n-butoxy group, a sec-butoxy group, a t-butoxy group, an n-pentyloxy group, and an n-hexyloxy group; and the like. Among these, a fluorine atom, a methoxy group, and an ethoxy group are preferable.

Examples of a substituent that may substitute the divalent aliphatic group having an alicyclic structure represented by $G_1$ and $G_2$ include halogen atoms such as a fluorine atom, a chlorine atom, a bromine atom, and an iodine atom; alkyl groups having 1 to 6 carbon atoms, a methyl group, an ethyl group, and a propyl group; alkoxy groups having 1 to 6 carbon atoms, such as a methoxy group, an ethoxy group, an n-propoxy group, an isopropoxy group, an n-butoxy group, a sec-butoxy group, a t-butoxy group, an n-pentyloxy group, and an n-hexyloxy group; and the like. Among these, a fluorine atom, a methoxy group, and an ethoxy group are preferable.

The aliphatic group optionally includes —O—, —S—, —O—C(=O)—, —C(=O)—O—, —O—C(=O)—O—, —NR²—C(=O)—, —C(=O)—NR²—, —NR²—, or —C(=O)—, provided that a case where the aliphatic group includes two or more adjacent —O— or —S— is excluded. R² is a hydrogen atom or an alkyl group having 1 to 6 carbon atoms similar to that represented by R¹, and is preferably a hydrogen atom or a methyl group.

—O—, —O—C(=O)—, —C(=O)—O—, and —C(=O)— are preferable as the group that is optionally included in the aliphatic group.

Specific examples of the aliphatic group that includes the above group include —CH₂—CH₂—O—CH₂—CH₂—, —CH₂—CH₂—S—CH₂—CH₂—, —CH₂—CH₂—O—C(=O)—CH₂—CH₂—, —CH₂—CH₂—C(=O)—O—CH₂—CH₂—, —CH₂—CH₂—C(=O)—O—CH₂—, —CH₂—O—C(=O)—O—CH₂—CH₂—, —CH₂—CH₂—NR²—C(=O)—CH₂—CH₂—, —CH₂—CH₂—C(=O)—NR²—CH₂—, —CH₂—NR²—CH₂—CH₂—, —CH₂—C(=O)—CH₂—, and the like.

It is preferable that G¹ and G² independently a divalent aliphatic group having a linear structure, such as an alkylene group having 1 to 12 carbon atoms or an alkenylene group having 1 to 12 carbon atoms, more preferably an alkylene group having 1 to 12 carbon atoms, such as a methylene group, an ethylene group, a trimethylene group, a propylene group, a tetramethylene group, a pentamethylene group, a hexamethylene group, or an octamethylene group, and particularly preferably a tetramethylene group (—(CH₂)₄—) or a hexamethylene group (—(CH₂)₆—), in order to ensure that the intended effects of the invention can be more advantageously achieved.

Z¹ and Z² are independently an alkenyl group having 2 to 10 carbon atoms that is unsubstituted, or substituted with a halogen atom.

The number of carbon atoms of the alkenyl group is preferably 2 to 6. Examples of the halogen atom that may substitute the alkenyl group represented by Z¹ and Z² include a fluorine atom, a chlorine atom, a bromine atom, and the like. Among these, a chlorine atom is preferable.

Specific examples of Z¹ and Z² include CH₂=CH—, CH₂=C(CH₃)—, CH₂=CH—CH₂—, CH₃—CH=CH—, CH₂=CH—CH₂—CH₂—, CH₂=C(CH₃)—CH₂—CH₂—, (CH₃)₂C=CH—CH₂—, (CH₃)₂C=CH—CH₂—CH₂—, CH₂=C(Cl)—, CH₂=C(CH₃)—CH₂—, CH₃—CH=CH—CH₂—, and the like.

It is preferable that Z¹ and Z² be independently CH₂=CH—, CH₂=C(CH₃)—, CH₂=C(Cl)—, CH₂=CH—CH₂—, CH₂=C(CH₃)—CH₂—, or CH₂=C(CH₃)—CH₂—CH₂—, more preferably CH₂=CH—, CH₂=C(CH₃)—, or CH₂=C(Cl)—, and particularly preferably CH₂=CH—, in order to ensure that the intended effects of the invention can be more advantageously achieved.

Aˣ is a fused ring group represented by the formula (II).

X in the formula (II) is —NR³—, an oxygen atom, a sulfur atom, —C(=O)—, —SO—, or —SO₂—. R³ is a hydrogen atom or an alkyl group having 1 to 6 carbon atoms similar to that represented by R¹. Among these, an oxygen atom and a sulfur atom preferable, and a sulfur atom is particularly preferable.

The part (hereinafter may be referred to as "ring D") represented by the following formula that is included the formula (II) is a substituted or unsubstituted ring having 1 to 20 carbon atoms that includes at least one nitrogen atom.

The ring D may be either a monocyclic ring or a fused ring. The ring D may be either a saturated ring or an unsaturated ring. The ring D may include a heteroatom (e.g., oxygen atom or sulfur atom) other than a nitrogen atom.

The total number of atoms included in the ring D is preferably 4 to 25.

Specific examples of the ring D include nitrogen-containing saturated heterocyclic rings obtained by substituting at least one carbon atom of an aliphatic saturated ring (e.g., cyclopentane ring, cyclohexane ring, cycloheptane ring, cyclooctane ring, or cyclodecane ring) with NR⁸ (wherein R⁸ is a hydrogen atom, an alkyl group having 1 to 6 carbon atoms, or a substituted or unsubstituted phenyl group); nitrogen-containing unsaturated heterocyclic rings obtained by substituting at least one carbon atom of an aromatic ring (e.g., benzene ring, naphthalene ring, phenanthrene ring, anthracene ring, pyrene ring, pentalene ring, indene ring, or azulene ring) with a nitrogen atom; nitrogen-containing heterocyclic rings including two or more heteroatoms and obtained by substituting at least one carbon atom of a heterocyclic ring that includes a heteroatom other than a nitrogen atom (e.g., oxetane ring, furan ring, thiophene ring, benzofuran ring, or benzothiophene ring) with NR⁸ (wherein R⁸ is the same as defined above); aromatic fused rings of an aromatic carbon ring and a nitrogen-containing heterocyclic ring (e.g., quinoline ring, quinoxaline ring, quinolizine ring, benzimidazole ring, benzoxazole ring, benzothiazole ring, and benzothiadiazole ring); and the like.

Examples of a substituent that may substitute the ring D include those mention later in connection with Rˣ.

Aˣ is preferably an aromatic fused ring group (fused ring group), and more preferably a fused ring group represented by the formula (II-1), a fused ring group represented by the formula (II-2), a fused ring group represented by the formula (II-3), a fused ring group represented by the formula (II-4), or a fused ring group represented by the formula (II-5) (provided that at least one (C—Rˣ) in each formula is substituted with a nitrogen atom).

It is preferable that one to three (C—Rˣ), and more preferable one (C—Rˣ) be substituted with a nitrogen atom.

Specific examples of the fused ring group represented by the formula (II-1), the fused ring group represented by the formula (II-2), the fused ring group represented by the formula (II-3), the fused ring group represented by the formula (II-4), and the fused ring group represented by the formula (II-5) (provided that at least one (C—Rˣ) in each formula is substituted with a nitrogen atom) are shown below. Note that the invention is not limited to the following examples.

(i) Specific examples of fused ring group represented by formula (II-1) (provided that at least one (C—Rˣ) is substituted with a nitrogen atom)

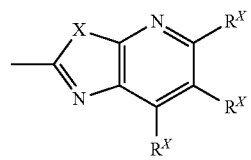

(II-1a)

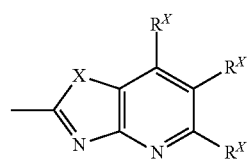

(II-1b)

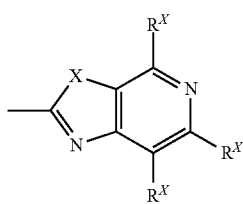
(II-1c)
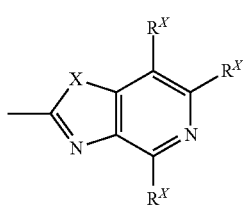
(II-1d)
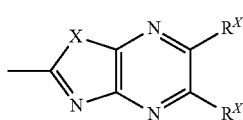
(II-1e)
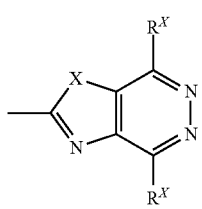
(II-1f)
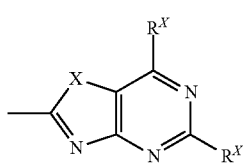
(II-1g)
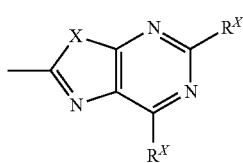
(II-1h)
(ii) Specific examples of fused ring group represented by formula (II-2) (provided that at least one (C—$R^X$) is substituted with a nitrogen atom)
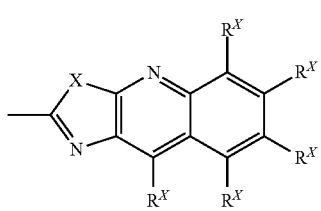
(II-2a)
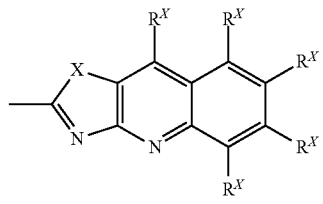
(II-2b)
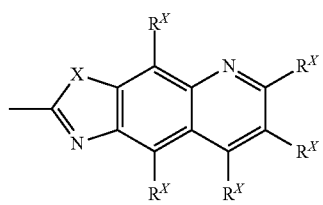
(II-2c)
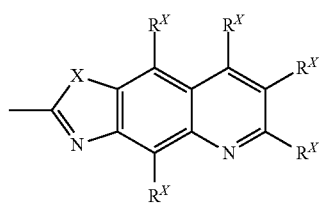
(II-2d)
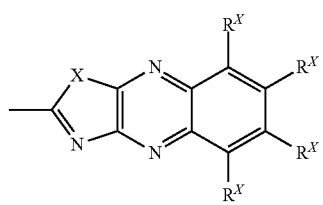
(II-2e)
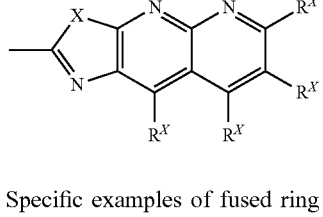
(II-2f)
(iii) Specific examples of fused ring group represented by formula (II-3) (provided that at least one (C—$R^X$) is substituted with a nitrogen atom)
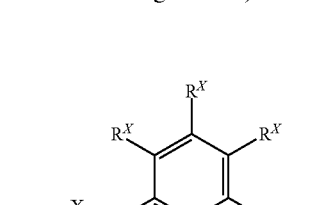
(II-3a)
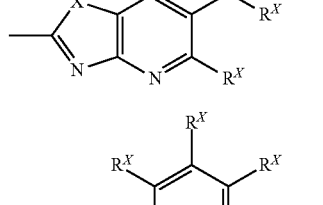
(II-3b)
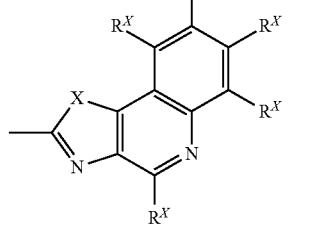

(II-3c)
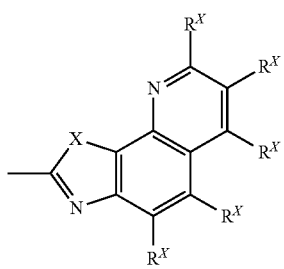
(II-3d)
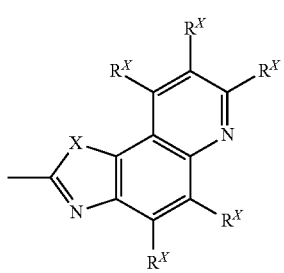
(iv) Specific examples of fused ring group represented by formula (II-4) (provided that at least one (C—R$^X$) is substituted with a nitrogen atom)
(II-4a)
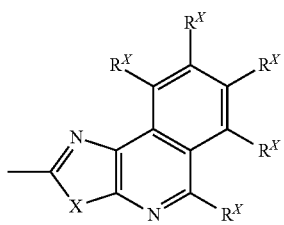
(II-4b)
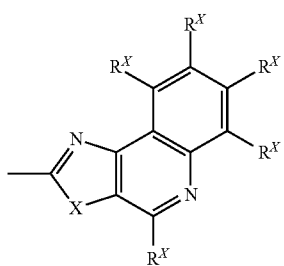
(II-4c)
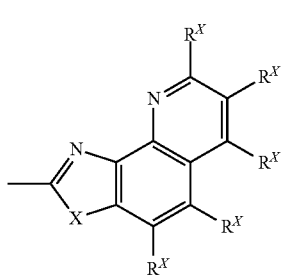
(II-4d)
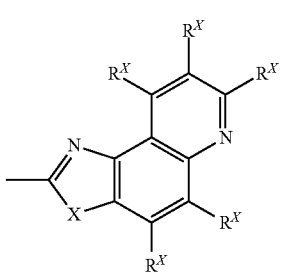
(v) Specific examples of fused ring group represented by formula (II-5) (provided that at least one (C—R$^X$) is substituted with a nitrogen atom)
(II-5a)
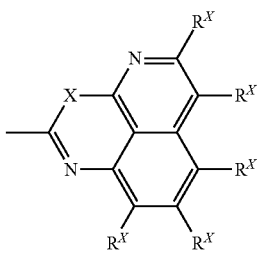
(II-5b)
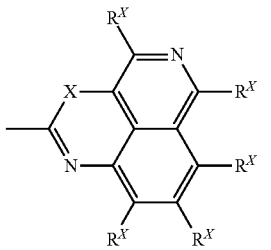
(II-5c)
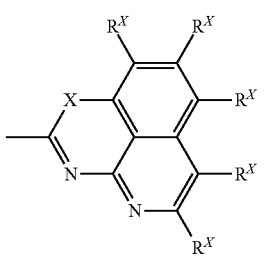
(II-5d)
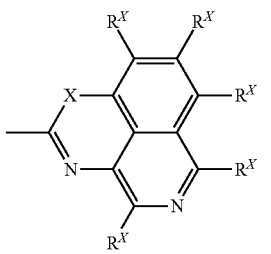

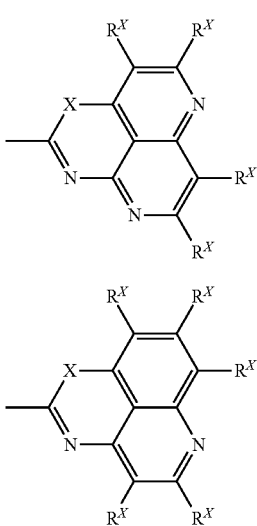

(II-5e)

(II-5f)

$R^X$ are a hydrogen atom, a halogen atom, an alkyl group having 1 to 6 carbon atoms, a cyano group, a nitro group, an alkylsulfinyl group having 1 to 6 carbon atoms, an alkylsulfonyl group having 1 to 6 carbon atoms, a fluoroalkyl group having 1 to 6 carbon atoms, an alkoxy group having 1 to 6 carbon atoms, an alkylthio group having 1 to 6 carbon atoms, a monosubstituted amino group, a disubstituted amino group, an alkylsulfamoyl group having 1 to 6 carbon atoms, a dialkylsulfamoyl group having 2 to 12 carbon atoms, or —C(=O)—O—$R^6$. $R^6$ is a hydrogen atom or an alkyl group having 1 to 6 carbon atoms similar to that represented by $R^1$. When a plurality of $R^X$ are present, the plurality of $R^X$ are either identical or different.

Examples of the halogen atom represented by $R^X$ include a fluorine atom, a chlorine atom, a bromine atom, and the like.

Examples of the alkyl group having 1 to 6 carbon atoms include a methyl group, an ethyl group, an n-propyl group, an isopropyl group, an n-butyl group, a t-butyl group, an n-pentyl group, an isopentyl group, an s-pentyl group, an n-hexyl group, and the like.

Examples of the alkylsulfinyl group having 1 to 6 carbon atoms include a methylsulfinyl group, an ethylsulfinyl group, a propylsulphinyl group, a butylsulfinyl group, and the like.

Examples of the alkylsulfonyl group having 1 to 6 carbon atoms include a methylsulfonyl group, an ethylsulfonyl group, a propylsulfonyl group, a butylsulfonyl group, and the like.

Examples of the fluoroalkyl group having 1 to 6 carbon atoms include a fluoromethyl group, a difluoromethyl group, a trifluoromethyl group, a fluoroethyl group, a 1,1-difluoroethyl group, a 1,2-difluoroethyl group, a 2,2,2-trifluoroethyl group, a pentafluoroethyl group, a 3,3,3-trifluoropropyl group, a perfluoropropyl group, and the like.

Examples of the alkoxy group having 1 to 6 carbon atoms include a methoxy group, an ethoxy group, an n-propoxy group, an isopropoxy group, an n-butoxy group, a t-butoxy group, and the like.

Examples of the alkylthio group having 1 to 6 carbon atoms include a methylthio group, an ethylthio group, an n-propylthio group, an isopropylthio group, an n-butylthio group, an isobutylthio group, an s-butylthio group, a t-butylthio group, and the like.

Examples of the monosubstituted amino group include monoalkylamino groups having 1 to 6 carbon atoms, such as a methylamino group, an ethylamino group, an n-propylamino group, an isopropylamino group, an n-butylamino group, an isobutylamino group, an s-butylamino group, and a t-butylamino group; arylamino groups such as a phenylamino group; acylimino groups such as an acetylamino group and a benzoylamino group; and the like.

Examples of the disubstituted amino group include dialkylamino groups having 1 to 6 carbon atoms, such as a dimethylamino group, a diethylamino group, a dipropylamino group, a dibutylamino group, a methylethylamino group, an ethylpropylamino group, a methylpropylamino group, and a methylbutylamino group; acylalkylamino groups having 1 to 6 carbon atoms, such as a methylacetylamino group and a methylbenzoylamino group; acylarylamino groups such as a phenylacethylamino group and a phenylbenzoylamino group; and the like.

Examples of the alkylsulfamoyl group having 1 to 6 carbon atoms include a methylsulfamoyl group, an ethylsulfamoyl group, and the like.

Examples of the dialkylsulfamoyl group having 2 to 12 carbon atoms include a dimethylsulfamoyl group, a diethylsulfamoyl group, and the like.

$R^X$ is preferably a hydrogen atom or an alkoxy group having 1 to 6 carbon atoms.

$A^x$ is more preferably a fused ring group represented by the formula (II-1), still more preferably a fused ring group represented by the following formula (II-1a) or a fused ring group represented by the following formula (II-1e), and particularly preferably a fused ring group represented by the following formula (II-1a1) or a fused ring group represented by the following formula (II-1e1), in order to ensure that the intended effects of the invention can be more advantageously achieved.

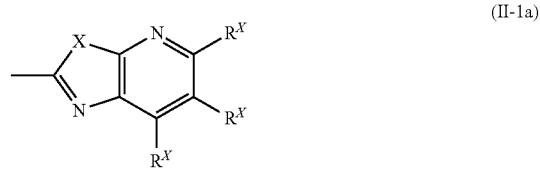

(II-1a)

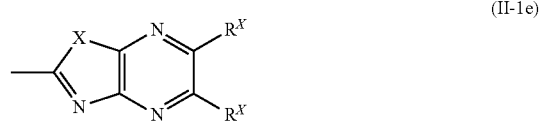

(II-1e)

wherein X and $R^X$ are the same as defined above.

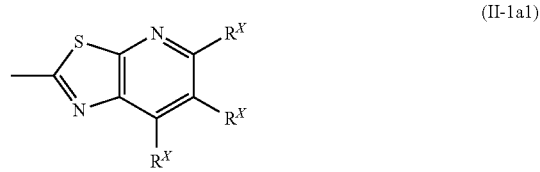

(II-1a1)

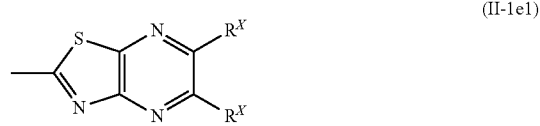

(II-1e1)

wherein $R^X$ is the same as defined above.

$A^y$ is a hydrogen atom, a substituted or unsubstituted alkyl group having 1 to 20 carbon atoms, a substituted or unsubstituted alkenyl group having 2 to 20 carbon atoms, a substituted or unsubstituted cycloalkyl group having 3 to 18 carbon atoms, —C(=O)—$R^4$, —$SO_2$—$R^5$, or an organic group having 2 to 30 carbon atoms that includes at least one aromatic ring selected from the group consisting of an aromatic hydrocarbon ring and an aromatic heterocyclic ring. $R^4$ is a substituted or unsubstituted alkyl group having 1 to 20 carbon atoms, a substituted or unsubstituted alkenyl group having 2 to 20 carbon atoms, or a substituted or unsubstituted cycloalkyl group having 3 to 18 carbon atoms, and $R^5$ is an alkyl group having 1 to 20 carbon atoms, an alkenyl group having 2 to 20 carbon atoms, a phenyl group, or a 4-methylphenyl group.

Examples of the alkyl group having 1 to 20 carbon atoms that forms the substituted or unsubstituted alkyl group having 1 to 20 carbon atoms represented by $A^y$ include a methyl group, an ethyl group, an n-propyl group, an isopropyl group, an n-butyl group, a sec-butyl group, a t-butyl group, an n-pentyl group, an isopentyl group, an n-hexyl group, an isohexyl group, an n-heptyl group, an isohexyl group, an n-octyl group, an n-nonyl group, an n-decyl group, an n-dodecyl group, an n-tridecyl group, an n-tetradecyl group, an n-pentadecyl group, an n-hexadecyl group, an n-heptadecyl group, an n-octadecyl group, an n-icosyl group, and the like. The number of carbon atoms of the substituted or unsubstituted alkyl group having 1 to 20 carbon atoms is preferably 1 to 6.

Examples of the alkenyl group having 2 to 20 carbon atoms that forms the substituted or unsubstituted alkenyl group having 2 to 20 carbon atoms represented by $A^y$ include a vinyl group, a propenyl group, an isopropenyl group, a butenyl group, a pentenyl group, a hexenyl group, a heptenyl group, an octenyl group, a decenyl group, a dodecenyl group, a tridecenyl group, a tetradecenyl group, a pentadecenyl group, a hexadecenyl group, a heptadecenyl group, an octadecenyl group, a nonadecenyl group, an icosenyl group, and the like. The number of carbon atoms of the substituted or unsubstituted alkenyl group having 2 to 20 carbon atoms is preferably 2 to 12.

Examples of the substituted or unsubstituted cycloalkyl group having 3 to 18 carbon atoms represented by $A^y$ include a cyclopropyl group, a cyclobutyl group, a cyclopentyl group, a cyclohexyl group, a cyclooctyl group, and the like.

Examples of a substituent that may substitute the substituted or unsubstituted alkyl group having 1 to 20 carbon atoms, the substituted or unsubstituted alkenyl group having 2 to 20 carbon atoms, and the substituted or unsubstituted cycloalkyl group having 3 to 18 carbon atoms represented by $A^y$ include halogen atoms such as a fluorine atom and a chlorine atom; a cyano group; substituted amino groups such as a dimethylamino group; alkoxy groups having 1 to 6 carbon atoms, such as a methoxy group, an ethoxy group, and an isopropoxy group; alkoxy groups having 1 to 6 carbon atoms substituted with an alkoxy group having 1 to 6 carbon atoms, such as a methoxymethoxy group and a methoxyethoxy group; a nitro group; aryl groups such as a phenyl group and a naphthyl group; cycloalkyl groups having 3 to 8 carbon atoms, such as a cyclopropyl group, a cyclopentyl group, and a cyclohexyl group; —C(=O)—$R^6$; —C(=O)—O$R^6$; —$SO_2R^6$; a hydroxyl group; and the like. Note that $R^6$ is the same as defined above.

Examples of the substituted or unsubstituted alkyl group having 1 to 20 carbon atoms, the substituted or unsubstituted alkenyl group having 2 to 20 carbon atoms, and the substituted or unsubstituted cycloalkyl group having 3 to 18 carbon atoms represented by $R^4$ include those mentioned above in connection with $A^y$.

Examples of the alkyl group having 1 to 20 carbon atoms and the alkenyl group having 2 to 20 carbon atoms represented by $R^5$ include those mentioned above in connection with $A^y$.

The organic group having 2 to 30 carbon atoms represented by $A^y$ that includes at least one aromatic ring selected from the group consisting of an aromatic hydrocarbon ring and an aromatic heterocyclic ring, may include a plurality of aromatic rings, and may include both an aromatic hydrocarbon ring and an aromatic heterocyclic ring.

Examples of the aromatic hydrocarbon ring include a benzene ring, a naphthalene ring, an anthracene ring, and the like. Examples of the aromatic heterocyclic ring include monocyclic aromatic heterocyclic rings such as a pyrrole ring, a furan ring, a thiophene ring, a pyridine ring, a pyridazine ring, a pyrimidine ring, a pyrazine ring, a pyrazole ring, an imidazole ring, an oxazole ring, and a thiazole ring; fused aromatic heterocyclic rings such as a benzothiazole ring, a benzoxazole ring, a quinoline ring, a phthalazine ring, a benzimidazole ring, a benzopyrazole ring, a benzofuran ring, a benzothiophene ring, and the fused ring represented by the formula (II); and the like.

The aromatic ring included in $A^y$ may be substituted with a substituent. Examples of the substituent include halogen atoms such as a fluorine atom and a chlorine atom; a cyano group; alkyl groups having 1 to 6 carbon atoms, such as a methyl group, an ethyl group, and a propyl group; alkenyl groups having 2 to 6 carbon atoms, such as a vinyl group and an allyl group; alkyl halide groups having 1 to 6 carbon atoms, such as a trifluoromethyl group; substituted amino groups such as a dimethylamino group; alkoxy groups having 1 to 6 carbon atoms, such as a methoxy group, an ethoxy group, and an isopropoxy group; a nitro group; aryl groups such as a phenyl group and a naphthyl group; —C(=O)—$R^6$; —C(=O)—O$R^6$; —$SO_2R^7$; and the like. Note that $R^6$ is the same as defined above. $R^7$ is an alkyl group having 1 to 6 carbon atoms (e.g., methyl group or ethyl group) or an aryl group having 6 to 14 carbon atoms (e.g., phenyl group, 1-naphthyl group, or 2-naphthyl group).

The aromatic ring included in $A^y$ may be substituted with a plurality of identical or different substituents, and two adjacent substituents may bond to each other to form a ring. A ring formed by two adjacent substituents may be either a monocyclic ring or a fused polycyclic ring.

Note that the number of carbon atoms (i.e., 2 to 30) of the organic group represented by $A^y$ refers to the total number of carbon atoms of the organic group excluding the number of carbon atoms of a substituent.

Examples of the organic group having 2 to 30 carbon atoms represented by $A^y$ that includes at least one aromatic ring selected from the group consisting of an aromatic hydrocarbon ring and an aromatic heterocyclic ring, include aromatic cyclic hydrocarbon groups; aromatic heterocyclic groups; alkyl groups having 3 to 30 carbon atoms that include at least one aromatic ring selected from the group consisting of an aromatic hydrocarbon ring and an aromatic heterocyclic ring; alkenyl groups having 4 to 30 carbon atoms that include at least one aromatic ring selected from the group consisting of an aromatic hydrocarbon ring and an aromatic heterocyclic ring; alkynyl groups having 4 to 30 carbon atoms that include at least one aromatic ring selected from the group consisting of an aromatic hydrocarbon ring and an aromatic heterocyclic ring; and the like.

$A^y$ is preferably a hydrogen atom, a substituted or unsubstituted alkyl group having 1 to 20 carbon atoms, a substituted or unsubstituted alkenyl group having 2 to 20 carbon atoms, a substituted or unsubstituted cycloalkyl group having 3 to 18 carbon atoms, —C(=O)—$R^4$, or —SO$_2$—$R^5$. Note that $R^4$ and $R^5$ are the same as defined above.

The total number of π electrons included in $A^x$ and $A^y$ is preferably 4 to 24, and more preferably 6 to 18, in order to ensure that the intended effects of the invention can be more advantageously achieved.

$A^1$ is a substituted or unsubstituted trivalent aromatic group. The trivalent aromatic group may be a trivalent carbocyclic aromatic group, or may be a trivalent heterocyclic aromatic group. It is preferable that the trivalent aromatic group be a trivalent carbocyclic aromatic group, more preferably a trivalent benzene ring group or a trivalent naphthalene ring group, and still more preferably a trivalent benzene ring group or a trivalent naphthalene ring group represented by the following formulas, in order to ensure that the intended effects of the invention can be more advantageously achieved.

Note that the substituents $Y^1$ and $Y^2$ are also shown in the following formulas so that the bonding state can be easily understood ($Y^1$ and $Y^2$ are the same as defined above (hereinafter the same)).

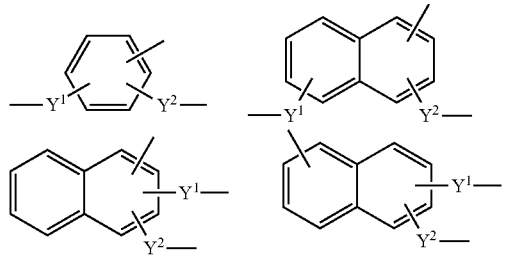

$A^1$ is more preferably a group among groups respectively represented by the following formulas (A11) to (A25), still more preferably a group among the groups respectively represented by the formulas (A11), (A13), (A15), (A19), and (A23), and particularly preferably the group represented by the formula (A11) or the group represented by the formula (A23).

(A11)

(A12)

(A13)

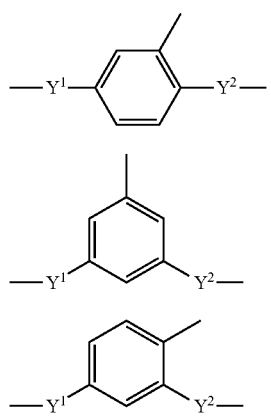

(A14)

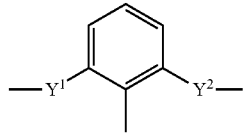

(A15)

(A16)

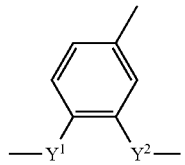

(A17)

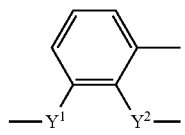

(A18)

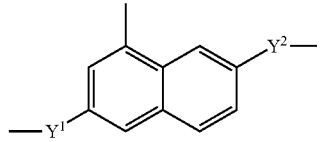

(A19)

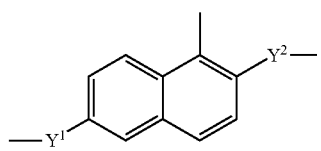

(A20)

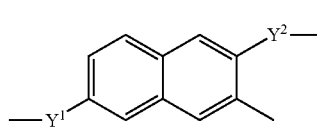

(A21)

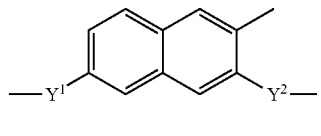

(A22)

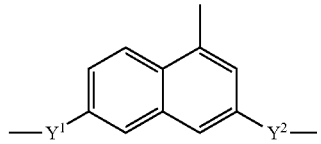

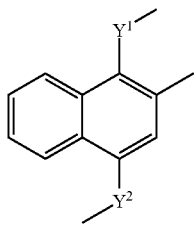
(A23)

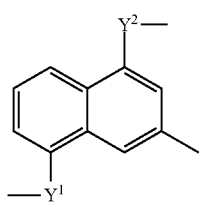
(A24)

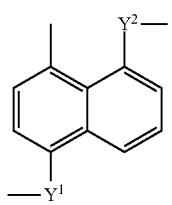
(A25)

Examples of a substituent that may substitute the trivalent aromatic group represented by $A^1$ include those mentioned above in connection with a substituent that may substitute the aromatic ring included in $A^y$. It is preferable that $A^1$ be unsubstituted.

$A^2$ and $A^3$ are independently a substituted or unsubstituted divalent aromatic group having 6 to 30 carbon atoms.

The aromatic group represented by $A^2$ and $A^3$ may be either a monocyclic aromatic group or a polycyclic aromatic group.

Specific examples of a preferable aromatic group represented by $A^2$ and $A^3$ include the following groups.

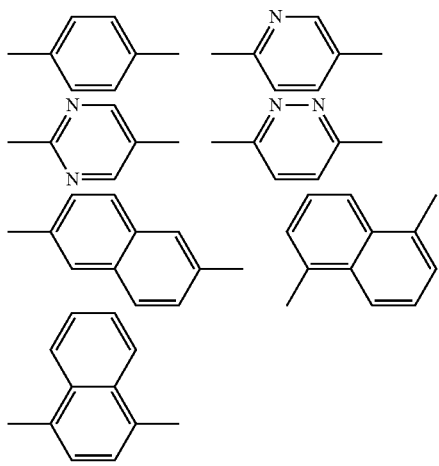

The aromatic group represented by $A^2$ and $A^3$ may be substituted with a substituent at an arbitrary position. Examples of the substituent include halogen atoms, a cyano group, a hydroxyl group, alkyl groups having 1 to 6 carbon atoms, alkoxy groups having 1 to 6 carbon atoms, a nitro group, a —C(═O)—OR group, and the like. Note that R is an alkyl group having 1 to 6 carbon atoms. Among these, a halogen atom, an alkyl group having 1 to 6 carbon atoms, or an alkoxy group having 1 to 6 carbon atoms are preferable as the substituent. A fluorine atom is preferable as the halogen atom. A methyl group, an ethyl group, and a propyl group are preferable as the alkyl group having 1 to 6 carbon atoms. A methoxy group and an ethoxy group are preferable as the alkoxy group having 1 to 6 carbon atoms.

It is preferable that $A^2$ and $A^3$ be independently the group represented by the following formula (A31), (A32), or (A33) that may be substituted with a substituent, and more preferably the group represented by the formula (A31) that may be substituted with a substituent, in order to ensure that the intended effects of the invention can be more advantageously achieved.

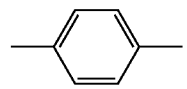
(A31)

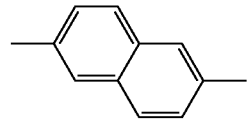
(A32)

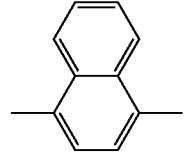
(A33)

$Q^1$ is a hydrogen atom, or a substituted or unsubstituted alkyl group having 1 to 6 carbon atoms.

Examples of the substituted or unsubstituted alkyl group having 1 to 6 carbon atoms include those mentioned above in connection with $A^x$.

$Q^1$ is preferably a hydrogen atom or an alkyl group having 1 to 6 carbon atoms, and more preferably a hydrogen atom or a methyl group.

The polymerizable compound according to one embodiment of the invention may be produced by effecting the following reaction, for example.

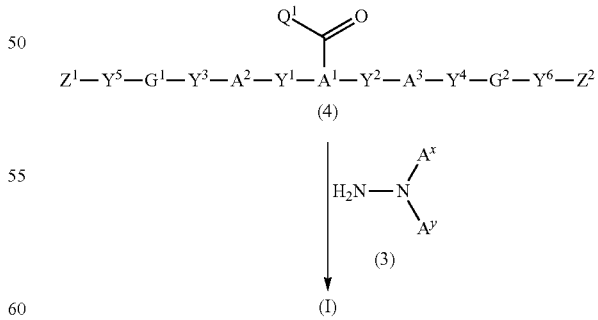

wherein $Y^1$ to $Y^6$, $G^1$, $G^2$, $Z^1$, $Z^2$, $A^x$, $A^y$, $A^1$ to $A^3$, and $Q^1$ are the same as defined above.

Specifically, the hydrazine compound represented by the formula (3) (hydrazine compound (3)) is reacted with the carbonyl compound represented by the formula (4) (carbonyl compound (4)) in a molar ratio (hydrazine compound (3):carbonyl compound (4)) of 1:2 to 2:1 (preferably 1:1.5 to 1.5:1) to produce the polymerizable compound represented by the formula (I) with high selectivity in high yield.

The above reaction may be effected in the presence of an acid catalyst such as an organic acid (e.g., (±)-10-camphorsulfonic acid or p-toluenesulfonic acid) or an inorganic acid (e.g., hydrochloric acid or sulfuric acid). The addition of the acid catalyst may reduce the reaction time, and improve the yield. The acid catalyst is normally added in an amount of 0.001 to 1 mol based on 1 mol of the carbonyl compound (4). The acid catalyst may be added directly, or may be added in the form of a solution prepared by dissolving the acid catalyst in an appropriate solvent.

The solvent used for the above reaction is not particularly limited as long as the solvent is inert to the reaction. Examples of the solvent include alcohol-based solvents such as methyl alcohol, ethyl alcohol, n-propyl alcohol, isopropyl alcohol, n-butyl alcohol, isobutyl alcohol, sec-butyl alcohol, and t-butyl alcohol; ether-based solvents such as diethyl ether, tetrahydrofuran, 1,2-dimethoxyethane, 1,4-dioxane, and cyclopentyl methyl ether; ester-based solvents such as ethyl acetate, propyl acetate, and methyl propionate; aromatic hydrocarbon-based solvents such as benzene, toluene, and xylene; aliphatic hydrocarbon-based solvents such as n-pentane, n-hexane, and n-heptane; amide-based solvents such as N,N-dimethylformamide, N-methylpyrrolidone, and hexamethylphosphoric triamide; sulfur-containing solvents such as dimethyl sulfoxide and sulfolane; mixed solvents of two or more solvents among these solvents; and the like.

Among these, alcohol-based solvents, ether-based solvents, and mixed solvents of an alcohol-based solvent and an ether-based solvent are preferable.

The solvent may be used in an appropriate amount taking account of the type of each compound, the reaction scale, and the like. The solvent is normally used in an amount of 1 to 100 g per gram of the hydrazine compound (3).

The reaction proceeds smoothly when the reaction temperature is within the range from −10° C. to the boiling point of the solvent. The reaction time is determined taking account of the reaction scale, but is normally several minutes to several hours.

The hydrazine compound (3) may be produced using a known method. For example, the hydrazine compound (3) may be produced as shown below.

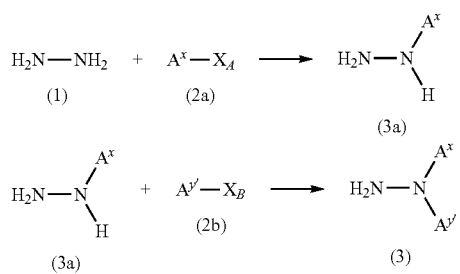

wherein $A^x$ is the same as defined above, $A^{y'}$ is the same as $A^y$, provided that a hydrogen atom is excluded, $X^A$ and $X^B$ are independently a leaving group (e.g., amino group, halogen atom, alkylthio group, alkylsulfonyloxy group, or arylsulfonyloxy group).

Specifically, the compound represented by the formula (2a) is reacted with the hydrazine (1) in an appropriate solvent in a molar ratio (compound (2a):hydrazine (1)) of 1:1 to 1:20 (preferably 1:2 to 1:10) to obtain the hydrazine compound (3a) in which $A^y$ is a hydrogen atom, and the hydrazine compound (3a) is reacted with the compound represented by the formula (2b) to obtain the hydrazine compound (3).

Hydrazine monohydrate is normally used as the hydrazine (1). A commercially available product may be used directly as the hydrazine (1).

The solvent used for the above reaction is not particularly limited as long as the solvent is inert to the reaction. Examples of the solvent include alcohol-based solvents such as methyl alcohol, ethyl alcohol, n-propyl alcohol, isopropyl alcohol, n-butyl alcohol, isobutyl alcohol, sec-butyl alcohol, and t-butyl alcohol; ether-based solvents such as diethyl ether, tetrahydrofuran, 1,2-dimethoxyethane, 1,4-dioxane, cyclopentyl methyl ether, and ethylene glycol; aromatic hydrocarbon-based solvents such as benzene, toluene, and xylene; aliphatic hydrocarbon-based solvents such as n-pentane, n-hexane, and n-heptane; amide-based solvents such as N,N-dimethylformamide, N-methylpyrrolidone, and hexamethylphosphoric triamide; sulfur-containing solvents such as dimethyl sulfoxide and sulfolane; mixed solvents of two or more solvents among these solvents; and the like.

Among these, alcohol-based solvents and ether-based solvents are preferable.

When $X_A$ is an amino group, it is preferable to react the compound (2a) and the hydrazine (1) in the presence of an acid (e.g., concentrated hydrochloric acid). The acid is preferably used in an amount of 1 equivalent based on the compound (2a).

The solvent may be used in an appropriate amount taking account of the type of each compound, the reaction scale, and the like. The solvent is normally used in an amount of 1 to 100 g per gram of hydrazine.

The reaction proceeds smoothly when the reaction temperature is within the range from −10° C. to the boiling point of the solvent. The reaction time is determined taking account of the reaction scale, but is normally several minutes to 10 hours.

The compound represented by the formula (3) may also be synthesized as shown below, for example.

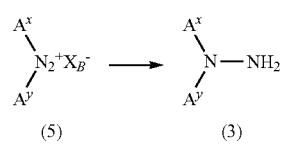

wherein $A^x$ and $A^y$ are the same as defined above, and $X_B^-$ is an anion that is a counter ion for diazonium. Examples of the anion represented by $X_B^-$ include inorganic anions such as a hexafluorophosphoric acid ion, a fluoroboric acid ion, a chloride ion, and a sulfuric acid ion; organic anions such as a polyfluoroalkylcarboxylic acid ion, a polyfluoroalkylsulfonic acid ion, a tetraphenylboric acid ion, an aromatic carboxylic acid ion, and an aromatic sulfonic acid ion; and the like.

Examples of a reducing agent used for the above reaction include a metal salt reducing agent.

The term "metal salt reducing agent" normally refers to a compound that includes a metal having a small valence, or a compound that includes a metal ion and a hydrido source (see "*Yuki Gosei Jikkenhou Handbook*" (Handbook of Organic Synthesis Experiments)", 1990, edited by The Society of Synthetic Organic Chemistry, Japan, published by Maruzen Co., Ltd., p. 810).

Examples of the metal salt reducing agent include $NaAlH_4$, $NaAlH_p(Or)_q$ (wherein p and q are independently an integer from 1 to 3, provided that p+q=4, and r is an alkyl group having 1 to 6 carbon atoms), $LiAlH_4$, $iBu_2AlH$, $LiBH_4$, $NaBH_4$, $SnCl_2$, $CrCl_2$, $TiCl_3$, and the like.

The reduction reaction may be effected under known reaction conditions. For example, the reduction reaction may be effected under the reaction conditions described in JP-A-2005-336103, "Shin-Jikken Kagaku Koza (New Experimental Chemistry Course)", 1978, Vol. 14, published by Maruzen Co., Ltd., "Jikken Kagaku Koza (Experimental Chemistry Course)", 1992, Vol. 20, published by Maruzen Co., Ltd., or the like.

The diazonium salt (5) may be produced from aniline or the like using a known method.

Many of the compounds (2a) are known compounds, and may be produced using a known method. For example, the compound (2a-1) in which $X_A$ is an amino group and X is a sulfur atom may be produced as shown below.

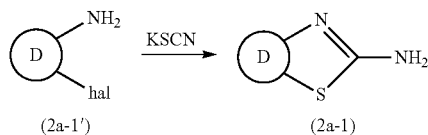

wherein D is the same as defined above, and hal is a halogen atom (e.g., chlorine atom or bromine atom).

Specifically, the compound (2a-1) may be produced by reacting the compound represented by the formula (2a-1') (compound (2a-1')) with potassium thiocyanate in an inert gas atmosphere (e.g., nitrogen atmosphere) in the presence of concentrated hydrochloric acid.

Concentrated hydrochloric acid is normally used in an amount of 3 to 30 mol, and preferably 5 to 15 mol, based on 1 g of the compound (2a-1').

Potassium thiocyanate is normally used in an amount of 1 to 3 mol, and preferably 1.2 to 2 mol, based on 1 mol of the compound (2a-1').

The reaction temperature is normally 60 to 150° C., and preferably 80 to 120° C. The reaction time is determined taking account of the reaction scale, but is normally several tens of minutes to several hours.

The compound (2a-1) may also be produced by reacting the compound represented by the formula (2a-1") (compound (2a-1")) with potassium thiocyanate and bromine in an inert gas atmosphere (e.g., nitrogen atmosphere) in the presence of acetic acid (see below).

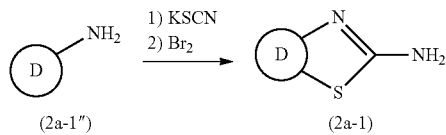

wherein D is the same as defined above.

Acetic acid is normally used in an amount of 0.1 to 10 mol, and preferably 1 to 5 mol, based on 1 g of the compound (2a-1").

Potassium thiocyanate is normally used in an amount of 1 to 20 mol, and preferably 3 to 10 mol, based on 1 mol of the compound (2a-1").

Bromine is normally used in an amount of 1 to 5 mol, and preferably 1 to 3 mol, based on 1 mol of the compound (2a-1").

The reaction temperature is normally −10 to +20° C., and preferably −5 to +10° C. The reaction time is determined taking account of the reaction scale, but is normally several tens of minutes to several hours.

The compound (2a-2) in which $X_A$ is an alkylthio group ($SR^4$) and X is a sulfur atom may be produced as shown below.

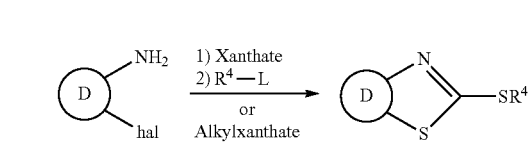

wherein D is the same as defined above, $R^4$ is an alkyl group (e.g., methyl group), and L is a leaving group (e.g., halogen atom).

Specifically, the compound (2a-2) (compound represented by the formula (2a-2)) may be produced by reacting the compound represented by the formula (2a-1') with a xanthate, and reacting the resulting product with the compound represented by $R^4$-L. The compound (2a-2) (compound represented by the formula (2a-2)) may also be produced by reacting the compound represented by the formula (2a-1') with an alkylxanthate.

The xanthate or the alkylxanthate is normally used in an amount of 1 to 5 mol, and preferably 1.5 to 3 mol, based on 1 mol of the compound (2a-1").

Specific examples of the xanthate include sodium xanthate, potassium xanthate, and the like. Specific examples of the alkylxanthate include sodium ethylxanthate, potassium ethylxanthate, potassium butylxanthate, potassium amylxanthate, and the like.

The compound represented by $R^4$-L is normally used in an amount of 0.5 to 3 mol, and preferably 1 to 2 mol, based on 1 mol of the xanthate.

Specific examples of the compound represented by $R^4$-L include methyl iodide and the like.

The above reaction proceeds smoothly when the reaction temperature is within the range from −10° C. to the boiling point of the solvent.

The carbonyl compound (4) may be produced by appropriately bonding and modifying a plurality of known compounds having a desired structure by arbitrarily combining an ether linkage (—O—)-forming reaction, an ester linkage (—C(=O)—O— or —O—C(=O)—)-forming reaction, a carbonate linkage (—O—C(=O)—O—)-forming reaction, and an amide linkage (—C(=O)—NH— or —NH—C (=O)—)-forming reaction.

An ether linkage may be formed as described below.
(i) A compound represented by D1-hal (wherein Hal is the same as defined above (hereinafter the same)) and a compound represented by D2-OMet (wherein Met is an alkali metal (mainly sodium) (hereinafter the same)) are mixed and condensed (Williamson synthesis). Note that D1 and D2 are an arbitrary organic group (hereinafter the same).
(ii) A compound represented by D1-hal and a compound represented by D2-OH are mixed and condensed in the presence of a base (e.g., sodium hydroxide or potassium hydroxide).

(iii) A compound represented by D1-J (wherein J is an epoxy group) and a compound represented by D2-OH are mixed and condensed in the presence of a base (e.g., sodium hydroxide or potassium hydroxide).

(iv) A compound represented by D1-OFN (wherein OFN is a group that includes an unsaturated bond) and a compound represented by D2-OMet are mixed and subjected to an addition reaction in the presence of a base (e.g., sodium hydroxide or potassium hydroxide).

(v) A compound represented by D1-hal and a compound represented by D2-OMet are mixed and condensed in the presence of copper or cuprous chloride (Ullmann condensation).

An ester linkage and an amide linkage may be formed as described below.

(vi) A compound represented by D1-COOH and a compound represented by D2-OH or D2-NH$_2$ are subjected to dehydration and condensation in the presence of a dehydration-condensation agent (e.g., N,N-dicyclohexylcarbodiimide).

(vii) A compound represented by D1-COOH is reacted with a halogenating agent to obtain a compound represented by D1-CO-hal, and the compound represented by D1-CO-hal is reacted with a compound represented by D2-OH or D2-NH$_2$ in the presence of a base.

(viii) A compound represented by D1-COOH is reacted with an acid anhydride to obtain a mixed acid anhydride, and the mixed acid anhydride is reacted with a compound represented by D2-OH or D2-NH$_2$.

(ix) A compound represented by D1-COOH and a compound represented by D2-OH or D2-NH$_2$ are subjected to dehydration and condensation in the presence of an acid catalyst or a base catalyst.

More specifically, the carbonyl compound (4) in which the group represented by $Z^2$—$Y^6$-$G^2$-$Y^4$-$A^3$-$Y^2$— is identical with the group represented by $Z^1$—$Y^5$-$G^1$-$Y^3$-$A^2$-$Y^1$—, and $Y^1$ is a group represented by $Y^{11}$—(=O)—O— (hereinafter referred to as "compound (4')") may be produced by the following reaction.

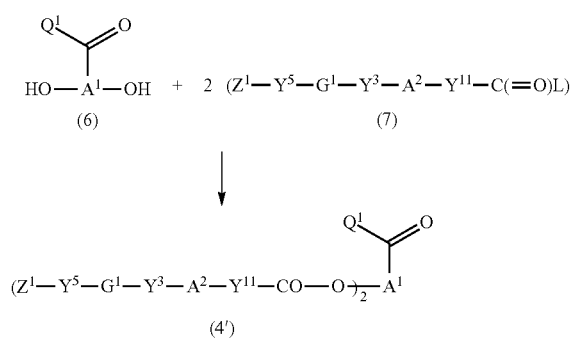

wherein $Y^3$, $Y^5$, $G^1$, $Z^1$, $A^1$, $A^2$, and $Q^1$ are the same as defined above, $Y^{11}$ a group whereby $Y^1$ is $Y^{11}$—C(=O)—O—, $Y^1$ is the same as defined above, and L is a leaving group (e.g., hydroxyl group, halogen atom, methanesulfonyloxy group, or p-toluenesulfonyloxy group).

Specifically, the dihydroxy compound represented by the formula (6) (compound (6)) is reacted with the compound represented by the formula (7) (compound (7)) in a molar ratio (compound (6):compound (7)) of 1:2 to 1:4 (preferably 1:2 to 1:3) to produce the target compound (4') with high selectivity in high yield.

When the compound (7) is a compound (carboxylic acid) represented by the formula (7) in which L is a hydroxyl group, the target product may be obtained by effecting the reaction in the presence of a dehydration-condensation agent (e.g., 1-ethyl-3-(3-dimethylaminopropyl)carbodiimide hydrochloride or dicyclohexylcarbodiimide).

The dehydration-condensation agent is normally used in an amount of 1 to 3 mol based on 1 mol of the compound (7).

When the compound (7) is a compound (acid halide) represented by the formula (7) in which L is a halogen atom, the target product may be obtained by effecting the reaction in the presence of a base.

Examples of the base include organic bases such as triethylamine and pyridine, and inorganic bases such as sodium hydroxide, sodium carbonate, and sodium hydrogen carbonate.

The base is normally used in an amount of 1 to 3 mol based on 1 mol of the compound (7).

When the compound (7) is a compound (mixed acid anhydride) represented by the formula (7) in which L is a methanesulfonyloxy group or a p-toluenesulfonyloxy group, the target product may be obtained in the same manner as in the case where L is a halogen atom.

Examples of the solvent used for the above reaction include chlorine-based solvents such as chloroform and methylene chloride; amide-based solvents such as N-methylpyrrolidone, N,N-dimethylformamide, N,N-dimethylacetamide, and hexamethylphosphoric triamide; ether-based solvents such as 1,4-dioxane, cyclopentyl methyl ether, tetrahydrofuran, tetrahydropyran, and 1,3-dioxolane; sulfur-containing solvents such as dimethyl sulfoxide and sulfolane; aromatic hydrocarbon-based solvents such as benzene, toluene, and xylene; aliphatic hydrocarbon-based solvents such as n-pentane, n-hexane, and n-octane; alicyclic hydrocarbon-based solvents such as cyclopentane and cyclohexane; mixed solvents of two or more solvents among these solvents; and the like.

The solvent may be used in an appropriate amount taking account of the type of each compound, the reaction scale, and the like. The solvent is normally used in an amount of 1 to 50 g per gram of the hydroxy compound (6).

Many of the compounds (6) are known compounds, and may be produced using a known method.

For example, 1,4-dihydroxy-2-formylnaphthalene (intermediate H (see the examples)) may be produced by the methods disclosed in WO2009/042544 and The Journal of Organic Chemistry, 2011, 76, 8082-8087 using 1,4-dimethoxynaphthalene (manufactured by Sigma-Aldrich) as a raw material.

Most of the compounds (7) are known compounds. The compound (7) may be produced by appropriately bonding and modifying a plurality of known compounds having the desired structure by arbitrarily combining an ether linkage (—O—)-forming reaction, an ester linkage (—C(=O)—O— or —O—C(=O)—)-forming reaction, a carbonate linkage (—O—C(=O)—O—)-forming reaction, and an amide linkage (—C(=O)—NH— or —NH—C(=O)—)-forming reaction.

A commercially available product may be used as the compound (6) or (7) optionally after purification.

The target product is isolated by performing a post-treatment operation normally employed in synthetic organic chemistry after completion of the reaction, optionally followed by a known purification/separation means such as column chromatography, recrystallization, or distillation.

The structure of the target product may be identified by measurement (e.g., NMR spectrometry, IR spectrometry, or mass spectrometry), elemental analysis, or the like.

2) Polymerizable Composition

A polymerizable composition according to one embodiment of the invention includes the polymerizable compound according to one embodiment of the invention, and an initiator. The initiator is used to more efficiently polymerize the polymerizable composition according to one embodiment of the invention.

The initiator may be appropriately selected taking account of the type of polymerizable group included in the polymerizable compound. For example, a radical initiator may be used when the polymerizable group is a radically polymerizable group. An anionic initiator may be used when the polymerizable group is an anionically polymerizable group. A cationic initiator may be used when the polymerizable group is a cationically polymerizable group.

Examples of the radical initiator include a thermal radical generator that is a compound that generates active species that initiate polymerization of the polymerizable compound upon heating, and a photo-radical generator that is a compound that generates active species that initiate polymerization of the polymerizable compound upon exposure to exposure light (e.g., visible rays, ultraviolet rays (e.g., i-line), deep ultraviolet rays, electron beams, or X-rays). It is preferable to use the photo-radical generator.

Examples of the photo-radical generator include acetophenone-based compounds, biimidazole-based compounds, triazine-based compounds, O-acyloxime-based compounds, onium salt-based compounds, benzoin-based compounds, benzophenone-based compounds, α-diketone-based compounds, polynuclear quinone-based compounds, xanthone-based compounds, diazo-based compounds, imide sulfonate-based compounds, and the like. These compounds generate active radicals and/or an active acid upon exposure. These photo-radical generators may be used either alone or in combination.

Specific examples of the acetophenone-based compounds include 2-hydroxy-2-methyl-1-phenylpropan-1-one, 2-methyl-1-[4-(methylthio)phenyl]-2-morpholinopropan-1-one, 2-benzyl-2-dimethylamino-1-(4-morpholinophenyl)butan-1-one, 1-hydroxycyclohexyl phenyl ketone, 2,2-dimethoxy-1,2-diphenylethan-1-one, 1,2-octanedione, 2-benzyl-2-dimethylamino-4'-morpholinobutyrophenone, and the like.

Specific examples of the biimidazole-based compounds include 2,2'-bis(2-chlorophenyl)-4,4',5,5'-tetrakis(4-ethoxycarbonylphenyl)-1,2'-biimidazole, 2,2'-bis(2-bromophenyl)-4,4',5,5'-tetrakis(4-ethoxycarbonylphenyl)-1,2'-biimidazole, 2,2'-bis(2-chlorophenyl)-4,4',5,5'-tetraphenyl-1,2'-biimidazole, 2,2'-bis(2,4-dichlorophenyl)-4,4',5,5'-tetraphenyl-1,2'-biimidazole, 2,2'-bis(2,4,6-trichlorophenyl)-4,4',5,5'-tetraphenyl-1,2'-biimidazole, 2,2'-bis(2-bromophenyl)-4,4',5,5'-tetraphenyl-1,2'-biimidazole, 2,2'-bis(2,4-dibromophenyl)-4,4',5,5'-tetraphenyl-1,2'-biimidazole, 2,2'-bis(2,4,6-tribromophenyl)-4,4',5,5'-tetraphenyl-1,2'-biimidazole, and the like.

When using a biimidazole-based compound as a photoinitiator, it is preferable to use a hydrogen donor in combination with the biimidazole-based compound since sensitivity can be further improved.

The term "hydrogen donor" used herein refers to a compound that can donate a hydrogen atom to radicals generated by the biimidazole-based compound upon exposure. A mercaptan-based compound, an amine-based compound, and the like are preferable as the hydrogen donor.

Examples of the mercaptan-based compound include 2-mercaptobenzothiazole, 2-mercaptobenzoxazole, 2-mercaptobenzimidazole, 2,5-dimercapto-1,3,4-thiadiazole, 2-mercapto-2,5-dimethylaminopyridine, and the like. Examples of the amine-based compound include 4,4'-bis(dimethylamino)benzophenone, 4,4'-bis(diethylamino)benzophenone, 4-dimethylaminoacetophenone, 4-dimethylaminopropiophenone, ethyl-4-dimethylaminobenzoate, 4-dimethylaminobenzoic acid, 4-dimethylaminobenzonitrile, and the like.

Specific examples of the triazine-based compounds include triazine-based compounds that include a halomethyl group, such as 2,4,6-tris(trichloromethyl)-s-triazine, 2-methyl-4,6-bis(trichloromethyl)-s-triazine, 2-[2-(5-methylfuran-2-yl)ethenyl]-4,6-bis(trichloromethyl)-s-triazine, 2-[2-(furan-2-yl)ethenyl]-4,6-bis(trichloromethyl)-s-triazine, 2-[2-(4-diethylamino-2-methylphenyl)ethenyl]-4,6-bis(trichloromethyl)-s-triazine, 2-[2-(3,4-dimethoxyphenyl)ethenyl]-4,6-bis(trichloromethyl)-s-triazine, 2-(4-methoxyphenyl)-4,6-bis(trichloromethyl)-s-triazine, 2-(4-ethoxystyryl)-4,6-bis(trichloromethyl)-s-triazine, and 2-(4-n-butoxyphenyl)-4,6-bis(trichloromethyl)-s-triazine.

Specific examples of the O-acyloxime-based compounds include 1-[4-(phenylthio)phenyl]-heptane-1,2-dione-2-(O-benzoyloxime), 1-[4-(phenylthio)phenyl]-octane-1,2-dione-2-(O-benzoyloxime), 1-[4-(benzoyl)phenyl]-octane-1,2-dione-2-(O-benzoyloxime), 1-[9-ethyl-6-(2-methylbenzoyl)-9h-carbazol-3-yl]-ethanone-1-(O-acetyloxime), 1-[9-ethyl-6-(3-methylbenzoyl)-9h-carbazol-3-yl]-ethanone-1-(O-acetyloxime), 1-(9-ethyl-6-benzoyl-9h-carbazol-3-yl)-ethanone-1-(O-acetyloxime), ethanone-1-[9-ethyl-6-(2-methyl-4-tetrahydrofuranylbenzoyl)-9H-carbazol-3-yl]-1-(O-acetyloxime), ethanone-1-[9-ethyl-6-(2-methyl-4-tetrahydropyranylbenzoyl)-9H-carbazol-3-yl]-1-(O-acetyloxime), ethanone-1-[9-ethyl-6-(2-methyl-5-tetrahydrofuranylbenzoyl)-9H-carbazol-3-yl]-1-(O-acetyloxime), ethanone-1-[9-ethyl-6-(2-methyl-5-tetrahydropyranylbenzoyl)-9H-carbazol-3-yl]-1-(O-acetyloxime), ethanone-1-[9-ethyl-6-{2-methyl-4-(2,2-dimethyl-1,3-dioxolanyl)benzoyl}-9H-carbazol-3-yl]-1-(O-acetyloxime), ethanone-1-[9-ethyl-6-(2-methyl-4-tetrahydrofuranylmethoxybenzoyl)-9H-carbazol-3-yl]-1-(O-acetyloxime), ethanone-1-[9-ethyl-6-(2-methyl-4-tetrahydropyranylmethoxybenzoyl)-9H-carbazol-3-yl]-1-(O-acetyloxime), ethanone-1-[9-ethyl-6-(2-methyl-5-tetrahydrofuranylmethoxybenzoyl)-9H-carbazol-3-yl]-1-(O-acetyloxime), ethanone-1-[9-ethyl-6-(2-methylbenzoyl)-9H-carbazol-3-yl]-1-(O-acetyloxime), ethanone-1-[9-ethyl-6-(2-methyl-5-tetrahydropyranylmethoxybenzoyl)-9H-carbazol-3-yl]-1-(O-acetyloxime), ethanone-1-[9-ethyl-6-{2-methyl-4-(2,2-dimethyl-1,3-dioxolanyl)methoxybenzoyl}-9H-carbazol-3-yl]-1-(O-acetyloxime), and the like.

A commercially available product may be used directly as the photo-radical generator. Specific examples of a commercially available photo-radical generator include Irgacure 907, Irgacure 184, Irgacure 369, Irgacure 651, Irgacure 819, Irgacure 907, Irgacure OXE02 (manufactured by BASF); Adekaoptomer N1919 (manufactured by Adeka Corporation); and the like.

Examples of the anionic initiator include alkyllithium compounds; monolithium salts or monosodium salts of biphenyl, naphthalene, pyrene, and the like; polyfunctional initiators such as dilithiums and trilithium salts; and the like.

Examples of the cationic initiator include proton acids such as sulfuric acid, phosphoric acid, perchloric acid, and trifluoromethanesulfonic acid; Lewis acids such as boron trifluoride, aluminum chloride, titanium tetrachloride, and tin tetrachloride; an aromatic onium salt or a combination of an aromatic onium salt and a reducing agent; and the like.

These initiators may be used either alone or in combination.

The initiator is normally used to prepare the polymerizable composition according to one embodiment of the invention in an amount of 0.1 to 30 parts by weight, and preferably 0.5 to 10 parts by weight, based on 100 parts by weight of the polymerizable compound.

It is preferable to add a surfactant to the polymerizable composition according to one embodiment of the invention in order to adjust the surface tension of the polymerizable composition. The surfactant is not particularly limited. A nonionic surfactant is normally preferable as the surfactant. A commercially available product may be used as the nonionic surfactant. Examples of the nonionic surfactant include a nonionic surfactant "KH-40" (manufactured by AGC Seimi Chemical Co., Ltd.) (i.e., an oligomer having a molecular weight of about several thousand), and the like.

The surfactant is normally added to the polymerizable composition according to one embodiment of the invention in an amount of 0.01 to 10 parts by weight, and preferably 0.1 to 2 parts by weight, based on 100 parts by weight of the polymerizable compound.

The polymerizable composition according to one embodiment of the invention may further include an additional additive such as an additional copolymerizable monomer, a metal, a metal complex, a dye, a pigment, a fluorescent material, a phosphorescent material, a leveling agent, a thixotropic agent, a gelling agent, a polysaccharide, a UV absorber, an IR (infrared) absorber, an antioxidant, an ion-exchange resin, or a metal oxide (e.g., titanium oxide).

Each additive is normally added to the polymerizable composition according to one embodiment of the invention in an amount of 0.1 to 20 parts by weight based on 100 parts by weight of the polymerizable compound.

The polymerizable composition according to one embodiment of the invention may be prepared by mixing and dissolving given amounts of the polymerizable compound according to one embodiment of the invention, the initiator, and an optional additive in an appropriate solvent.

Examples of the solvent include ketones such as cyclopentanone, cyclohexanone, and methyl ethyl ketone; acetates such as butyl acetate and amyl acetate; halogenated hydrocarbons such as chloroform, dichloromethane, and dichloroethane; ethers such as 1,4-dioxane, cyclopentyl methyl ether, tetrahydrofuran, tetrahydropyran, and 1,3-dioxolane; and the like.

The polymerizable composition thus obtained is useful as a raw material for producing a polymer or an optically anisotropic article according to the embodiments of the invention (described below).

3) Polymer

A polymer according to one embodiment of the invention is (1) a polymer obtained by polymerizing the polymerizable compound according to one embodiment of the invention, or (2) a polymer obtained by polymerizing the polymerizable composition according to one embodiment of the invention.

The term "polymerization" used herein refers to a chemical reaction in a broad sense including a normal polymerization reaction and a crosslinking reaction.

(1) Polymer Obtained by Polymerizing Polymerizable Compound

The polymer obtained by polymerizing the polymerizable compound according to one embodiment of the invention may be a homopolymer of the polymerizable compound according to one embodiment of the invention, a copolymer of two or more types of the polymerizable compound according to one embodiment of the invention, or a copolymer of the polymerizable compound according to one embodiment of the invention and an additional copolymerizable monomer.

Examples of the additional copolymerizable monomer include, but are not limited to, 4'-methoxyphenyl 4-(2-methacryloyloxyethyloxyl)benzoate, biphenyl 4-(6-methacryloyloxyhexyloxyl)benzoate, 4'-cyanobiphenyl 4-(2-acryloyloxyethyloxyl)benzoate, 4'-cyanobiphenyl 4-(2-methacryloyloxyethyloxyl)benzoate, 3',4'-difluorophenyl 4-(2-methacryloyloxyethyloxyl)benzoate, naphthyl 4-(2-methacryloyloxyethyloxyl)benzoate, 4-acryloyloxy-4'-decylbiphenyl, 4-acryloyloxy-4'-cyanobiphenyl, 4-(2-acryloyloxyethyloxy)-4'-cyanobiphenyl, 4-(2-methacryloyloxyethyloxy)-4'-methoxybiphenyl, 4-(2-methacryloyloxyethyloxy)-4'-(4"-fluorobenzyloxy)-biphenyl, 4-acryloyloxy-4'-propylcyclohexylphenyl, 4-methacryloyl-4'-butylbicyclohexyl, 4-acryloyl-4'-amyltolan, 4-acryloyl-4'-(3,4-difluorophenyl)bicyclohexyl, (4-amylphenyl) 4-(2-acryloyloxyethyl)benzoate, (4-(4'-propylcyclohexyl)phenyl) 4-(2-acryloyloxyethyl)benzoate, and the like.

Examples of a commercially available product of the additional copolymerizable monomer include LC-242 (manufactured by BASF) and the like. The compounds disclosed in JP-A-2007-002208, JP-A-2009-173893, JP-A-2009-274984, JP-A-2010-030979, JP-A-2010-031223, JP-A-2011-006360, and the like may be used as the additional copolymerizable monomer.

A polyfunctional monomer that includes a plurality of polymerizable unsaturated groups (e.g., acryloyl group, methacryloyl group, vinyl group, and allyl group) may also be used as the additional copolymerizable monomer.

Examples of such a polyfunctional monomer include alkanediol diacrylates such as 1,2-butanediol diacrylate, 1,4-butanediol diacrylate, 1,3-butanediol diacrylate, neopentanediol diacrylate, and 1,6-hexanediol diacrylate, alkanediol dimethacrylates such as 1,2-butanediol dimethacrylate, 1,3-butanediol dimethacrylate, 1,4-butanediol dimethacrylate, neopentanediol dimethacrylate, and 1,6-hexanediol dimethacrylate, polyethylene glycol diacrylates such as ethylene glycol diacrylate, diethylene glycol diacrylate, triethylene glycol diacrylate, and tetraethylene glycol diacrylate, polypropylene glycol diacrylates such as propylene glycol diacrylate, dipropylene glycol diacrylate, tripropylene glycol diacrylate, and tetrapropylene glycol diacrylate, polyethylene glycol dimethacrylates such as ethylene glycol dimethacrylate, diethylene glycol dimethacrylate, triethylene glycol dimethacrylate, and tetraethylene glycol dimethacrylate, polypropylene glycol dimethacrylates such as propylene glycol dimethacrylate, dipropylene glycol dimethacrylate, tripropylene glycol dimethacrylate, and tetrapropylene glycol dimethacrylate, polyethylene glycol divinyl ethers such as ethylene glycol divinyl ether, diethylene glycol divinyl ether, triethylene glycol divinyl ether, and tetraethylene glycol divinyl ether, polyethylene glycol diallyl ethers such as ethylene glycol diallyl ether, diethylene glycol diallyl ether, triethylene glycol diallyl ether, and tetraethylene glycol diallyl ether, bisphenol F ethoxylate diacrylate, bisphenol F ethoxylate dimethacrylate, bisphenol A ethoxylate diacrylate, bisphenol A ethoxylate dimethacrylate, trimethylolpropane triacrylate, trimethylolpropane trimethacrylate, trimethylolpropane ethoxylate triacrylate, trimethylolpropane ethoxylate trimethacrylate, trimethylolpropane propoxylate triacrylate, trimethylolpropane propoxylate trimethacrylate, isocyanuric acid ethoxylate triacrylate, glycerol ethoxylate triacrylate, glycerol propoxylate triacrylate, pentaerythritol ethoxylate tetraacrylate, ditrimethylolpropane ethoxylate tetraacrylate, dipentaerythritol ethoxylate hexacrylate, and the like.

It is also possible to use a polymerizable compound that has a structure similar to that of the polymerizable compound represented by the formula (I) wherein $A^x$ is not the group represented by the formula (II).

The polymerizable compound according to one embodiment of the invention may be (co)polymerized optionally together with the additional copolymerizable monomer in the presence of an appropriate initiator. The initiator may be used in an amount similar to that of the initiator included in the polymerizable composition.

When the polymer according to one embodiment of the invention is a copolymer of the polymerizable compound according to one embodiment of the invention and the additional copolymerizable monomer, the content of structural units derived from the polymerizable compound according to one embodiment of the invention is not particularly limited, but is preferably 50 wt % or more, and more preferably 70 wt % or more, based on the total structural units. When the content of structural units derived from the polymerizable compound is within the above range, a polymer that has a high glass transition temperature (Tg) and high hardness can be obtained.

The polymer (1) may be produced by (A) (co)polymerizing the polymerizable compound optionally together with the additional copolymerizable monomer in an appropriate organic solvent in the presence of an appropriate initiator, isolating the target polymer, dissolving the polymer in an appropriate organic solvent to prepare a solution, applying the solution to an appropriate substrate to obtain a film, and drying the film, followed by optional heating, or (B) applying a solution prepared by dissolving the polymerizable compound in an organic solvent optionally together with the additional copolymerizable monomer to a substrate using a known coating method, removing the solvent, and effecting polymerization by applying heat or activated energy rays, for example.

Examples of the initiator include those mentioned above in connection with the initiator included in the polymerizable composition.

The organic solvent used for polymerization when using the method (A) is not particularly limited as long as the organic solvent is inert. Examples of the organic solvent include aromatic hydrocarbons such as toluene, xylene, and mesitylene; ketones such as cyclohexanone, cyclopentanone, and methyl ethyl ketone; acetates such as butyl acetate and amyl acetate; halogenated hydrocarbons such as chloroform, dichloromethane, and dichloroethane; ethers such as cyclopentyl methyl ether, tetrahydrofuran, and tetrahydropyran; and the like. Among these, it is preferable to use a compound having a boiling point of 60 to 250° C., and preferably 60 to 150° C., from the viewpoint of handling capability.

Examples of the organic solvent used to dissolve the polymer in the method (A) and the organic solvent used for the method (B) include ketone-based solvents such as acetone, methyl ethyl ketone, methyl isobutyl ketone, cyclopentanone, and cyclohexanone; ester-based solvents such as butyl acetate and amyl acetate; halogenated hydrocarbon-based solvents such as dichloromethane, chloroform, and dichloroethane; ether-based solvents such as tetrahydrofuran, tetrahydropyran, 1,2-dimethoxyethane, 1,4-dioxane, cyclopentyl methyl ether, 1,3-dioxolane; aprotic polar solvents such as N,N-dimethylformamide, N,N-dimethylacetamide, dimethyl sulfoxide, γ-butyrolactone, and N-methylpyrrolidone; and the like. Among these, it is preferable to use a compound having a boiling point of 60 to 200° C. from the viewpoint of handling capability. These solvents may be used either alone or in combination.

A substrate formed of a known organic or inorganic material may be used as the substrate. Examples of the organic material include polycycloolefins (e.g., Zeonex and Zeonor (registered trademark; manufactured by Zeon Corporation); Afton (registered trademark; manufactured by JSR Corporation); and Apel (registered trademark; manufactured by Mitsui Chemicals Inc.)), polyethylene terephthalate, polycarbonate, polyimide, polyamide, polymethyl methacrylate, polystyrene, polyvinyl chloride, polytetrafluoroethylene, cellulose, cellulose triacetate, polyethersulfone, and the like. Examples of the inorganic material include silicon, glass, calcite, and the like. It is preferable to use an organic material.

The substrate may be a single-layer substrate, or may be a laminate.

The substrate is preferably a substrate formed of an organic material, and more preferably a resin film formed of the organic material.

The polymer solution (method (A)) or the solution that is subjected to polymerization (method (B)) may be applied to the substrate using a known coating method. Examples of the coating method include a curtain coating method, an extrusion coating method, a roll coating method, a spin coating method, a dip coating method, a bar coating method, a spray coating method, a slide coating method, a print coating method, and the like.

(2) Polymer Obtained by Polymerizing Polymerizable Composition

The polymer according to one embodiment of the invention can be easily obtained by polymerizing the polymerizable composition according to one embodiment of the invention. It is preferable to use the polymerizable composition that includes the initiator (particularly a photoinitiator) in order to implement more efficient polymerization.

It is preferable to produce the polymer according to one embodiment of the invention using the method (B) that applies the polymerizable composition according to one embodiment of the invention to a substrate, and polymerizes the applied polymerizable composition. Examples of the substrate include a substrate used to produce an optically anisotropic article (described later), and the like.

The polymerizable composition according to one embodiment of the invention may be applied to the substrate using a known coating method (e.g., bar coating method, spin coating method, roll coating method, gravure coating method, spray coating method, die coating method, cap coating method, or dipping method). A known organic solvent may be added to the polymerizable composition according to one embodiment of the invention in order to improve the applicability of the polymerizable composition. In this case, it is preferable to remove the organic solvent by natural drying, drying by heating, drying under reduced pressure, drying by heating under reduced pressure, or the like after applying the polymerizable composition to the substrate.

The polymerizable compound according to one embodiment of the invention or the polymerizable composition according to one embodiment of the invention may be polymerized by applying activated energy rays, or utilizing a thermal polymerization method, for example. It is preferable to polymerize the polymerizable compound or the polymerizable composition by applying activated energy rays since heating is unnecessary (i.e., the reaction can be effected at room temperature). It is preferable to apply light (e.g., ultraviolet rays) to the polymerizable compound or the polymerizable composition from the viewpoint of convenience.

The temperature during application is preferably 30° C. or less. The dose is normally 1 W/m² to 10 kW/m², and preferably 5 W/m² to 2 kW/m².

A polymer obtained by polymerizing the polymerizable compound according to one embodiment of the invention or the polymerizable composition according to one embodiment of the invention may be removed from the substrate, and used alone, or may be used directly as an optical film organic material or the like without removing the polymer from the substrate.

The number average molecular weight of the polymer according to one embodiment of the invention thus obtained is preferably 500 to 500,000, and more preferably 5000 to 300,000. When the number average molecular weight of the polymer is within the above range, the resulting film exhibits high hardness and an excellent handling capability. The number average molecular weight of the polymer may be determined by gel permeation chromatography (GPC) using monodisperse polystyrene as a standard (eluant: tetrahydrofuran).

It is considered that the polymer according to one embodiment of the invention has a structure in which crosslinking points are uniformly present within the molecule, and exhibits a high crosslinking efficiency and excellent hardness.

The polymer according to one embodiment of the invention makes it possible to inexpensively produce an optical film that achieves uniform conversion of polarized light over a wide wavelength band, and exhibits satisfactory performance.

4) Optically Anisotropic Article

An optically anisotropic article according to one embodiment of the invention includes the polymer according to one embodiment of the invention.

The optically anisotropic article according to one embodiment of the invention may be obtained by forming an alignment film on a substrate, and forming a liquid crystal layer on the alignment film using the polymer according to one embodiment of the invention.

The alignment film is formed on the surface of the substrate in order to achieve in-plane alignment of an organic semiconductor compound in one direction.

The alignment film may be obtained by applying a solution (alignment film composition) that includes a polymer (e.g., polyimide, polyvinyl alcohol, polyester, polyallylate, polyamideimide, or polyetherimide) to the substrate to form a film, drying the film, and subjecting the film to a rubbing treatment in one direction, for example.

The thickness of the alignment film is preferably 0.001 to 5 μm, and more preferably 0.001 to 1 μm.

The rubbing treatment may be performed on the alignment film or the substrate. The rubbing treatment may be implemented using an arbitrary method. For example, the alignment film may be rubbed in a given direction using a roll around which a cloth or felt formed of synthetic fibers (e.g., nylon) or natural fibers (e.g., cotton) is wound. It is preferable to wash the alignment film with isopropyl alcohol or the like after the rubbing treatment in order to remove fine powder (foreign substances) formed during the rubbing treatment to clean the surface of the alignment film.

The alignment film may be provided with a function of achieving in-plane alignment in one direction by applying polarized UV rays to the surface of the alignment film.

The liquid crystal layer may be formed on the alignment film using the polymer according to one embodiment of the invention by utilizing the method described above in connection with the polymer according to one embodiment of the invention.

Since the optically anisotropic article according to one embodiment of the invention is produced using the polymer according to one embodiment of the invention, the optically anisotropic article can be produced at low cost, achieves uniform conversion of polarized light over a wide wavelength band, and exhibits satisfactory performance.

Examples of the optically anisotropic article according to one embodiment of the invention include a retardation film, an alignment film for liquid crystal display elements (liquid crystal displays), a polarizer, a viewing angle enhancement film, a color filter, a low-pass filter, an optical polarization prism, an optical filter, and the like.

EXAMPLES

The invention is further described below by way of examples. Note that the invention is not limited to the following examples.

Example 1

Synthesis of Compound 1

Compound 1

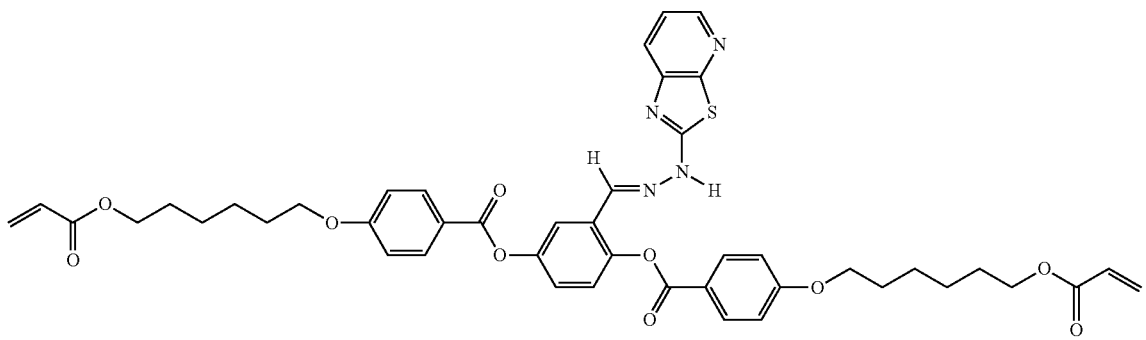

Step 1: Synthesis of Intermediate A

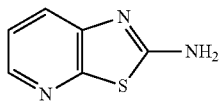

Intermediate A

A four-necked reactor equipped with a thermometer was charged with 3.00 g (23.3 mmol) of 3-amino-2-chloropyridine and 30 ml of concentrated hydrochloric acid under a nitrogen stream to prepare a homogeneous solution. After the addition of 3.40 g (35.0 mmol) of potassium thiocyanate to the solution, the mixture was stirred at 100° C. for 4 hours. After completion of the reaction, the reaction mixture was cooled to 20° C., followed by addition of 30 ml of water. The resulting solution was added to 100 ml of a saturated sodium carbonate aqueous solution while cooling the solution with ice to precipitate a solid, which was filtered off. The solid was washed with water, and dried using a vacuum dryer to obtain 2.11 g of an intermediate A as a light yellow solid (yield: 59.9%).

The structure of the target product was identified by $^1$H-NMR.

$^1$H-NMR (500 MHz, DMSO-$d_6$, TMS, δ ppm): 8.11 (dd, 1H, J=1.5 Hz, 5.0 Hz), 7.82 (s, 2H), 7.63 (dd, 1H, J=1.5 Hz, 8.0 Hz), 7.25 (dd, 1H, J=5.0 Hz, 8.0 Hz)

Step 2: Synthesis of Intermediate B

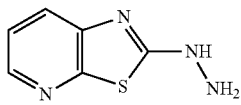

Intermediate B

A four-necked reactor equipped with a thermometer was charged with 1.50 g (9.92 mmol) of the intermediate A synthesized in the step 1, 2.4 ml (49.6 mmol) of hydrazine monohydrate, 0.8 ml (9.92 mmol) of concentrated hydrochloric acid, and 10 ml of ethylene glycol under a nitrogen stream to prepare a homogeneous solution. The solution was stirred at 140° C. for 6 hours. After completion of the reaction, the reaction mixture was cooled to 20° C., followed by addition of 20 ml of water to precipitate a solid, which was filtered off. The solid was washed with water, and dried using a vacuum dryer to obtain 1.47 g of an intermediate B as a yellow solid (yield: 89.2%).

The structure of the target product was identified by $^1$H-NMR.

$^1$H-NMR (400 MHz, DMSO-$d_6$, TMS, δ ppm): 9.30 (brs, 1H), 8.02 (dd, 1H, J=1.4 Hz, 5.0 Hz), 7.54 (dd, 1H, J=1.4 Hz, 8.1 Hz), 7.18 (dd, 1H, J=5.0 Hz, 8.1 Hz), 5.09 (s, 2H)

Step 3: Synthesis of Intermediate C

A four-necked reactor equipped with a thermometer was charged with 20 g (144.8 mmol) of 2,5-dihydroxybenzaldehyde, 105.8 g (362.0 mmol) of 4-(6-acryloylhex-1-yloxy)benzoic acid (manufactured by DKSH Japan K.K.), 5.3 g (43.4 mmol) of 4-(dimethylamino)pyridine, and 200 ml of N-methylpyrrolidone under a nitrogen stream to prepare a homogeneous solution. After the addition of 83.3 g (434.4 mmol) of 1-ethyl-3-(3-dimethylaminopropyl)carbodiimide hydrochloride (hereinafter referred to as "WSC") to the solution, the mixture was stirred at 25° C. for 12 hours. After completion of the reaction, the reaction mixture was added to 1.5 l of water, and extracted with 500 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a light yellow solid. The light yellow solid was purified by silica gel column chromatography (toluene:ethyl acetate=9:1 (volume ratio (hereinafter the same))) to obtain 75 g of an intermediate C as a white solid (yield: 75.4%).

The structure of the target product was identified by $^1$H-NMR.

$^1$H-NMR (400 MHz, CDCl$_3$, TMS, δ ppm): 10.20 (s, 1H), 8.18-8.12 (m, 4H), 7.78 (d, 1H, J=2.8 Hz), 7.52 (dd, 1H, J=2.8 Hz, 8.7 Hz), 7.38 (d, 1H, J=8.7 Hz), 7.00-6.96 (m, 4H), 6.40 (dd, 2H, J=1.4 Hz, 17.4 Hz), 6.12 (dd, 2H, J=10.6 Hz, 17.4 Hz), 5.82 (dd, 2H, J=1.4 Hz, 10.6 Hz), 4.18 (t, 4H, J=6.4 Hz), 4.08-4.04 (m, 4H), 1.88-1.81 (m, 4H), 1.76-1.69 (m, 4H), 1.58-1.42 (m, 8H)

Step 4: Synthesis of Compound 1

A four-necked reactor equipped with a thermometer was charged with 544 mg (3.28 mmol) of the intermediate B synthesized in the step 2, 1.50 g (2.18 mmol) of the intermediate C synthesized in the step 3, 10 ml of ethanol, and 10 ml of tetrahydrofuran (THF) under a nitrogen stream to prepare a homogeneous solution. After the addition of one drop of concentrated hydrochloric acid to the solution, the mixture was stirred at 25° C. for 5 hours. After completion of the reaction, the reaction mixture was added to 100 ml of water to precipitate a solid, which was filtered off. The solid was washed with water, and dried using a vacuum dryer to obtain 2.11 g of a grayish white solid. The grayish white solid was purified by silica gel column chromatography (toluene:ethyl acetate=70:30) to obtain 1.06 g of a compound 1 as a grayish white solid (yield: 58.2%).

The structure of the target product was identified by $^1$H-NMR.

$^1$H-NMR (500 MHz, DMSO-$d_6$, TMS, δ ppm): 12.61 (s, 1H), 8.24 (s, 1H), 8.20 (d, 1H, J=4.5 Hz), 8.16 (d, 2H, J=9.0 Hz), 8.13 (d, 2H, J=9.0 Hz), 7.77-7.82 (m, 2H), 7.46 (d, 1H, J=8.5 Hz), 7.43 (dd, 1H, J=2.5 Hz, 8.5 Hz), 7.33 (dd, 1H, J=4.5 Hz, 7.5 Hz), 7.17 (d, 2H, J=9.0 Hz), 7.14 (d, 2H, J=9.0 Hz), 6.33 (dd, 2H, J=1.5 Hz, 17.5 Hz), 6.18 (dd, 2H, J=10.0 Hz, 17.5 Hz), 5.94 (dd, 2H, J=1.5 Hz, 10.0 Hz), 4.13 (t, 4H, J=7.0 Hz), 4.12 (t, 4H, J=7.0 Hz), 1.75-1.81 (m, 4H), 1.63-1.69 (m, 4H), 1.38-1.51 (m, 8H)

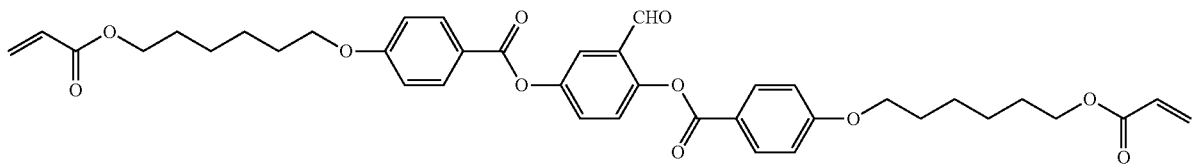

Intermediate C

Example 2

Synthesis of Compound 2

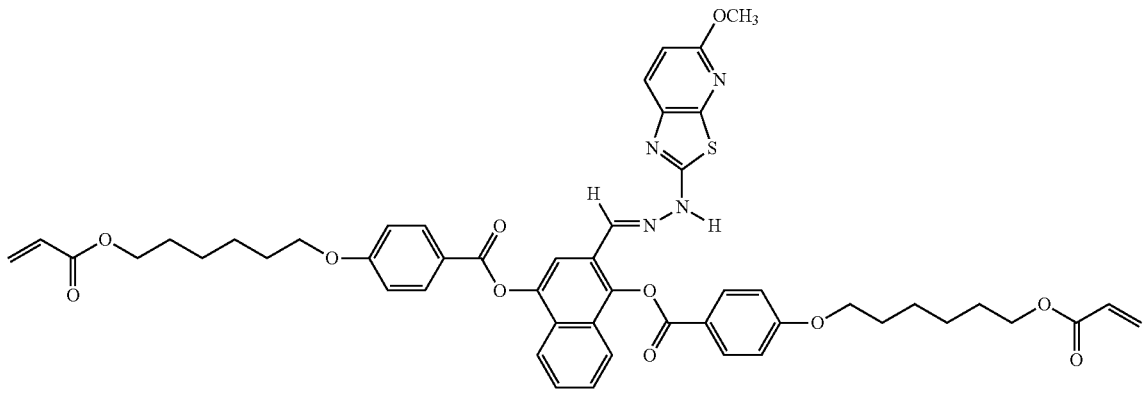

Compound 2

Step 1: Synthesis of Intermediate D

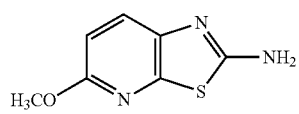

Intermediate D

A four-necked reactor equipped with a thermometer was charged with 2.50 g (20.1 mmol) of 5-amino-2-methoxypyridine and 5 ml of acetic acid under a nitrogen stream to prepare a homogeneous solution. After the addition of 9.82 g (101 mmol) of potassium thiocyanate dissolved in 50 ml of acetic acid to the solution, 1.5 ml (30.2 mmol) of bromine dissolved in 3 ml of acetic acid was added dropwise to the mixture at 0° C., and the mixture was stirred at 0° C. for 2 hours. After completion of the reaction, the reaction mixture was added to 300 ml of a saturated sodium hydrogen carbonate aqueous solution while cooling the reaction mixture with ice, and extracted with 500 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain 2.04 g of an intermediate D as a yellow solid (yield: 56.0%).

The structure of the target product was identified by $^1$H-NMR.

$^1$H-NMR (500 MHz, DMSO-$d_6$, TMS, δ ppm): 7.61 (d, 1H, J=8.5 Hz), 7.43 (s, 2H), 6.69 (d, 1H, J=8.5 Hz), 3.83 (s, 3H)

Step 2: Synthesis of Intermediate E

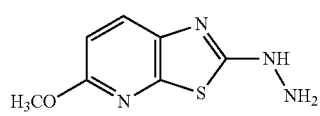

Intermediate E

A four-necked reactor equipped with a thermometer was charged with 2.00 g (11.0 mmol) of the intermediate D synthesized in the step 1, 2.6 ml (55.2 mmol) of hydrazine monohydrate, 0.5 ml (5.52 mmol) of concentrated hydrochloric acid, and 10 ml of ethylene glycol under a nitrogen stream to prepare a homogeneous solution. The solution was stirred at 140° C. for 5 hours. After completion of the reaction, the reaction mixture was cooled to 20° C., followed by addition of 20 ml of water to precipitate a solid, which was filtered off. The solid was washed with water, and dried using a vacuum dryer to obtain 666 mg of an intermediate E as a yellow solid (yield: 30.7%).

The structure of the target product was identified by $^1$H-NMR.

$^1$H-NMR (500 MHz, DMSO-$d_6$, TMS, δ ppm): 8.97 (s, 1H), 7.60 (d, 1H, J=8.5 Hz), 6.68 (d, 1H, J=8.5 Hz), 5.03 (s, 2H), 3.84 (s, 3H)

Step 3: Synthesis of Intermediate F

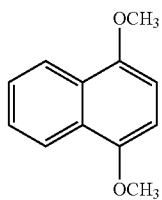

Intermediate F

A four-necked reactor equipped with a thermometer was charged with 20.0 g (125 mmol) of 1,4-dihydroxynaphthalene and 200 ml of N,N-dimethylformamide (DMF) under a nitrogen stream to prepare a homogeneous solution. After the addition of 51.8 g (375 mmol) of potassium carbonate and 19.4 ml (312 mmol) of methyl iodide, the mixture was stirred at 25° C. for 20 hours. After completion of the reaction, the reaction mixture was filtered through celite. The filtrate was added to 500 ml of water, and extracted with 500 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a white solid. The white solid was recrystallized from n-hexane (125 ml) to obtain 20.3 g of an intermediate F as colorless crystals (yield: 86.3%).

The structure of the target product was identified by $^1$H-NMR.

$^1$H-NMR (500 MHz, CDCl$_3$, TMS, δ ppm): 8.19-8.22 (m, 2H), 7.52-7.48 (m, 2H), 6.69 (s, 2H), 3.95 (s, 6H)

Step 4: Synthesis of Intermediate G

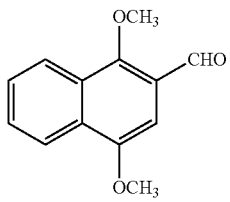

Intermediate G

A four-necked reactor equipped with a thermometer was charged with 15.0 g (79.7 mmol) of the intermediate F synthesized in the step 3 and 100 ml of dichloromethane under a nitrogen stream to prepare a homogeneous solution. After the addition of 91.7 g (91.7 mmol) of titanium tetrachloride (1.0 M dichloromethane solution) and 8.11 ml (91.7 mmol) of dichloromethyl methyl ether dropwise to the solution, the mixture was stirred at 0° C. for 1 hour. After completion of the reaction, the reaction mixture was added to 300 ml of ice water, and extracted with 500 ml of ethyl acetate. After drying the ethyl acetate layer over anhydrous magnesium sulfate, magnesium sulfate was separated by filtration. Ethyl acetate was evaporated from the filtrate under reduced pressure using a rotary evaporator to obtain a white solid. The white solid was recrystallized from n-hexane (260 ml) to obtain 16.6 g of an intermediate G as colorless crystals (yield: 96.4%).

The structure of the target product was identified by $^1$H-NMR.

$^1$H-NMR (500 MHz, CDCl$_3$, TMS, δ ppm): 10.58 (s, 1H), 8.28-8.31 (m, 1H), 8.20-8.22 (m, 1H), 7.61-7.67 (m, 2H), 7.13 (s, 1H), 4.10 (s, 3H), 4.03 (s, 3H)

Step 5: Synthesis of Intermediate H

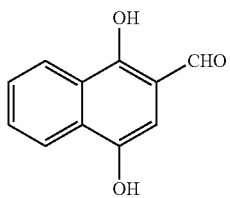

Intermediate H

A four-necked reactor equipped with a thermometer was charged with 16.6 g (76.8 mmol) of the intermediate G synthesized in the step 4 and 100 ml of dichloromethane under a nitrogen stream to prepare a homogeneous solution. The solution was cooled to −40° C. After the addition of 230 ml (230 mmol) of boron tribromide (17% dichloromethane solution) dropwise to the solution, the mixture was stirred at 25° C. for 2 hours. After completion of the reaction, the reaction mixture was added to 500 ml of ice water, and extracted with 500 ml of dichloromethane. After drying the dichloromethane layer over anhydrous magnesium sulfate, magnesium sulfate was separated by filtration. Dichloromethane was evaporated from the filtrate under reduced pressure using a rotary evaporator to obtain a yellow solid. The yellow solid was purified by silica gel column chromatography (n-hexane:ethyl acetate=70:30) to obtain 12.7 g of an intermediate H as a yellow solid (yield: 87.9%).

The structure of the target product was identified by $^1$H-NMR.

$^1$H-NMR (500 MHz, CDCl$_3$, TMS, δ ppm): 12.31 (s, 1H), 9.88 (s, 1H), 8.45 (d, 1H, J=8.5 Hz), 8.16 (d, 1H, J=8.5 Hz), 7.72 (dd, 1H, J=7.8 Hz, 8.5 Hz), 7.61 (dd, 1H, J=7.8 Hz, 8.5 Hz), 6.83 (s, 1H), 5.17 (s, 1H)

Step 6: Synthesis of Intermediate I

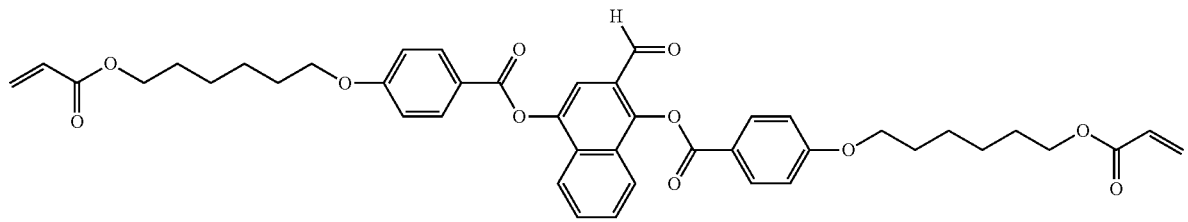

Intermediate I

A four-necked reactor equipped with a thermometer was charged with 2.00 g (10.6 mmol) of the intermediate H synthesized by the step 5, 7.78 g (26.6 mmol) of 4-(6-acryloylhex-1-yloxy)benzoic acid (manufactured by DKSH Japan K.K.), 648 mg (5.32 mmol) of 4-(dimethylamino) pyridine, and 30 ml of N-methylpyrrolidone under a nitrogen stream to prepare a homogeneous solution. After the addition of 6.63 g (31.8 mmol) of WSC to the solution, the mixture was stirred at 25° C. for 8 hours. After completion of the reaction, the reaction mixture was added to 300 ml of water, and extracted with 500 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a yellow solid. The yellow solid was purified by silica gel column chromatography (toluene:ethyl acetate=90:10) to obtain 3.38 g of an intermediate I as a yellow solid (yield: 43.2%).

The structure of the target product was identified by $^1$H-NMR.

$^1$H-NMR (400 MHz, DMSO-d$_6$, TMS, δ ppm): 10.33 (s, 1H), 8.30 (d, 2H, J=8.7 Hz), 8.26 (d, 2H, J=8.7 Hz), 8.04 (d, 1H, J=8.7 Hz), 7.99 (d, 1H, J=8.2 Hz), 7.85 (s, 1H), 7.66 (dd, 1H, J=6.9 Hz, 8.2 Hz), 7.59 (dd, 1H, J=6.9 Hz, 8.7 Hz), 7.06 (d, 2H, J=8.7 Hz), 7.03 (d, 2H, J=8.7 Hz), 6.41 (dd, 2H, J=1.4 Hz, 17.4 Hz), 6.13 (dd, 2H, J=10.4 Hz, 17.4 Hz), 5.82 (dd, 2H, J=1.4 Hz, 10.4 Hz), 4.19 (t, 4H, J=6.7 Hz), 4.10 (t, 2H, J=6.4 Hz), 4.08 (t, 2H, J=6.0 Hz), 1.81-1.89 (m, 4H), 1.70-1.77 (m, 4H), 1.46-1.60 (m, 8H)

Step 4: Synthesis of Compound 2

A four-necked reactor equipped with a thermometer was charged with 666 mg (3.40 mmol) of the intermediate E synthesized in the step 2, 1.67 g (2.26 mmol) of the intermediate I synthesized in the step 6, 20 ml of 1-propanol, and 20 ml of THF under a nitrogen stream to prepare a homogeneous solution. After the addition of one drop of concentrated hydrochloric acid to the solution, the mixture was stirred at 25° C. for 3.5 hours. After completion of the reaction, the reaction mixture was added to 300 ml of water to precipitate a solid, which was filtered off. The solid was washed with water, and dried using a vacuum dryer to obtain a yellow solid. The yellow solid was purified by silica gel column chromatography (toluene:ethyl acetate=70:30) to obtain 1.38 g of a compound 2 as a yellow solid (yield: 66.7%).

The structure of the target product was identified by $^1$H-NMR.

$^1$H-NMR (500 MHz, DMSO-d$_6$, TMS, δ ppm): 12.45 (s, 1H), 8.32 (s, 1H), 8.28 (d, 2H, J=9.0 Hz), 8.25 (d, 2H, J=9.0 Hz), 7.90-7.93 (m, 2H), 7.86-7.89 (m, 1H), 7.80 (d, 1H, J=7.0 Hz), 7.65-7.69 (m, 2H), 7.23 (d, 2H, J=9.0 Hz), 7.19 (d, 2H, J=9.0 Hz), 6.78 (d, 1H, J=8.5 Hz), 6.338 (dd, 1H, J=1.5 Hz, 17.5 Hz), 6.335 (dd, 1H, J=1.5 Hz, 17.5 Hz), 6.191 (dd, 1H, J=10.5 Hz, 17.5 Hz), 6.188 (dd, 1H, J=10.5 Hz, 17.5 Hz), 5.95 (dd, 1H, J=1.5 Hz, 10.5 Hz), 5.94 (dd, 1H, J=1.5 Hz, 10.5 Hz), 4.12-4.16 (m, 8H), 3.85 (s, 3H), 1.77-1.82 (m, 4H), 1.64-1.69 (m, 4H), 1.40-1.52 (m, 8H)

Example 3

Synthesis of Compound 3

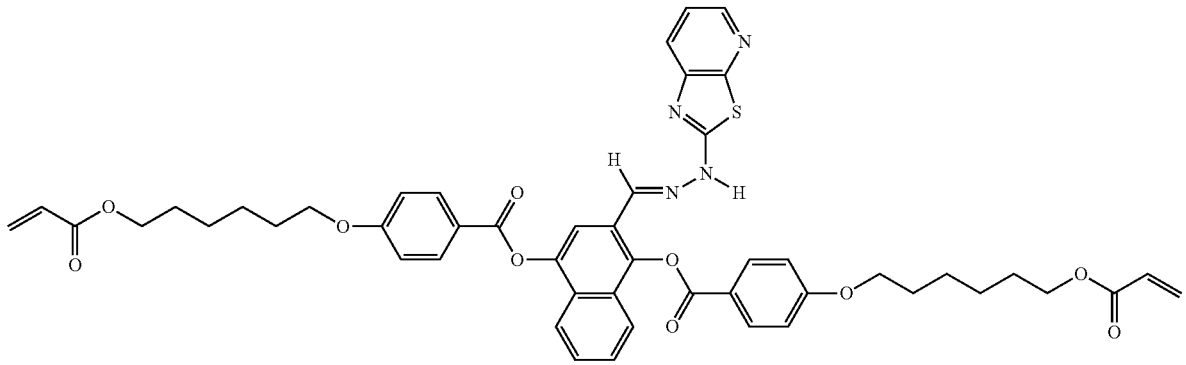

Compound 3

A four-necked reactor equipped with a thermometer was charged with 1.66 g (2.25 mmol) of the intermediate I synthesized in the step 6 of Example 2, 561 mg (3.38 mmol) of the intermediate B synthesized in the step 2 of Example 1, 10 ml of ethanol, and 10 ml of THF under a nitrogen stream to prepare a homogeneous solution. After the addition of one drop of concentrated hydrochloric acid to the solution, the mixture was stirred at 25° C. for 3.5 hours. After completion of the reaction, the reaction mixture was added to 200 ml of water to precipitate a solid, which was filtered off. The solid was washed with water, and dried using a vacuum dryer to obtain a yellow solid. The (light) yellow solid was purified by silica gel column chromatography (toluene:ethyl acetate=70:30) to obtain 1.01 g of a compound 3 as a light yellow solid (yield: 50.7%).

The structure of the target product was identified by $^1$H-NMR.

$^1$H-NMR (500 MHz, DMSO-d$_6$, TMS, δ ppm): 12.67 (brs, 1H), 8.40 (s, 1H), 8.30 (d, 2H, J=9.0 Hz), 8.26 (d, 2H, J=9.0 Hz), 8.22 (d, 1H, J=4.5 Hz), 7.94 (s, 1H), 7.88-7.93 (m, 2H), 7.77-7.85 (m, 1H), 7.67-7.70 (m, 2H), 7.34 (dd, 1H, J=4.5 Hz, 8.0 Hz), 7.24 (d, 2H, J=9.0 Hz), 7.21 (d, 2H, J=8.5 Hz), 6.34 (dd, 2H, J=1.5 Hz, 17.5 Hz), 6.20 (dd, 2H, J=10.5, 17.5 Hz), 5.95 (dd, 2H, J=1.5 Hz, 10.5 Hz), 4.13-4.18 (m, 8H), 1.77-1.82 (m, 4H), 1.65-1.70 (m, 4H), 1.40-1.53 (m, 8H)

Example 4

Synthesis of Compound 4

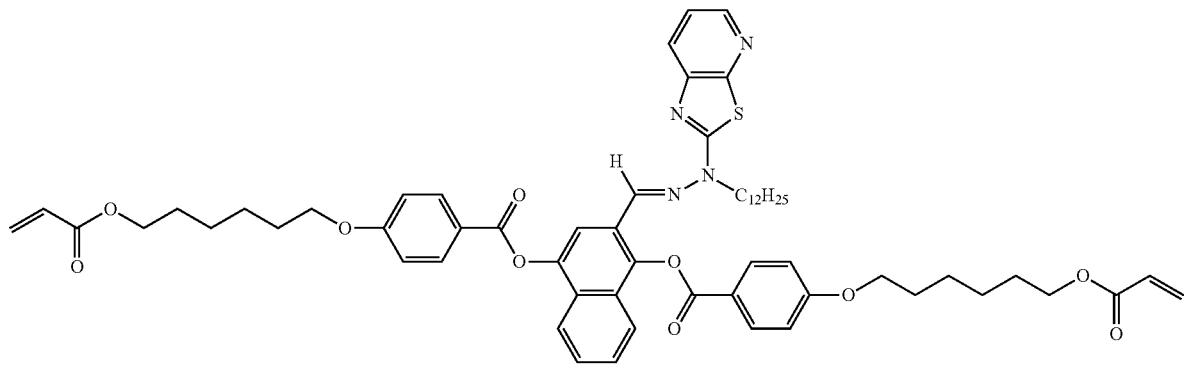

Compound 4

Step 1: Synthesis of Intermediate J

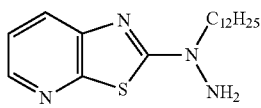

Intermediate J

A four-necked reactor equipped with a thermometer was charged with 2.24 g (13.5 mmol) of the intermediate B synthesized in the step 2 of Example 1 and 30 ml of DMF under a nitrogen stream to prepare a homogeneous solution. After the addition of 9.53 g (27.0 mmol) of cesium carbonate and 4.80 g (16.2 mmol) of 1-iodododecane to the solution, the mixture was stirred at room temperature for 20 hours. After completion of the reaction, the reaction mixture was added to 200 ml of water, and extracted with 300 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a yellow solid. The yellow solid was purified by silica gel column chromatography (toluene:ethyl acetate=80:20) to obtain 1.55 g of an intermediate J as a white solid (yield: 34.3%).

The structure of the target product was identified by $^1$H-NMR.

$^1$H-NMR (400 MHz, CDCl$_3$, TMS, δ ppm): 8.17 (d, 1H, J=4.6 Hz), 7.67 (d, 1H, J=8.2 Hz), 7.49 (dd, 1H, J=4.6 Hz, 8.2 Hz), 4.25 (s, 2H), 3.76 (t, 2H, J=6.9 Hz), 1.71-1.75 (m, 2H), 1.19-1.36 (m, 18H), 0.87 (t, 3H, J=6.6 Hz)

Step 2: Synthesis of Compound 4

A four-necked reactor equipped with a thermometer was charged with 436 mg (1.30 mmol) of the intermediate J synthesized in the step 1, 960 mg (1.30 mmol) of the intermediate I synthesized in the step 6 of Example 2, 5 ml of ethanol, and 10 ml of THF under a nitrogen stream to prepare a homogeneous solution. After the addition of 30.2 mg (0.13 mmol) of (±)-10-camphorsulfonic acid to the solution, the mixture was stirred at 40° C. for 2 hours. After completion of the reaction, the reaction mixture was added to 100 ml of saturated sodium bicarbonate water, and extracted twice with 100 ml of ethyl acetate. The ethyl acetate layer was collected, and dried over anhydrous sodium sulfate, and sodium sulfate was separated by filtration. Ethyl acetate was evaporated from the filtrate under reduced pressure using a rotary evaporator to obtain a yellow solid. The yellow solid was purified by silica gel column chromatography (toluene:ethyl acetate=90:10) to obtain 1.02 g of a compound 4 as a light yellow solid (yield: 74.5%).

The structure of the target product was identified by $^1$H-NMR.

$^1$H-NMR (500 MHz, CDCl$_3$, TMS, δ ppm): 8.32 (d, 4H, J=8.5 Hz), 8.25 (dd, 1H, J=1.5 Hz, 4.5 Hz), 8.04 (s, 1H), 7.89-7.97 (m, 3H), 7.80 (dd, 1H, J=1.5 Hz, 8.0 Hz), 7.51-7.56 (m, 2H), 7.22 (dd, 1H, J=4.5 Hz, 8.0 Hz), 7.07 (d, 4H, J=8.5 Hz), 6.42 (dd, 2H, J=1.0 Hz, 17.5 Hz), 6.14 (dd, 2H, J=10.5 Hz, 17.5 Hz), 5.84 (dd, 2H, J=1.0 Hz, 10.5 Hz) 4.16-4.22 (m, 6H), 4.11 (t, 2H, J=6.5 Hz), 4.09 (t, 2H, J=6.5 Hz), 1.86-1.92 (m, 4H), 1.73-1.78 (m, 4H), 1.47-1.65 (m, 10H), 1.06-1.33 (m, 18H), 0.88 (t, 3H, J=6.5 Hz)

Example 5

Synthesis of Compound 5

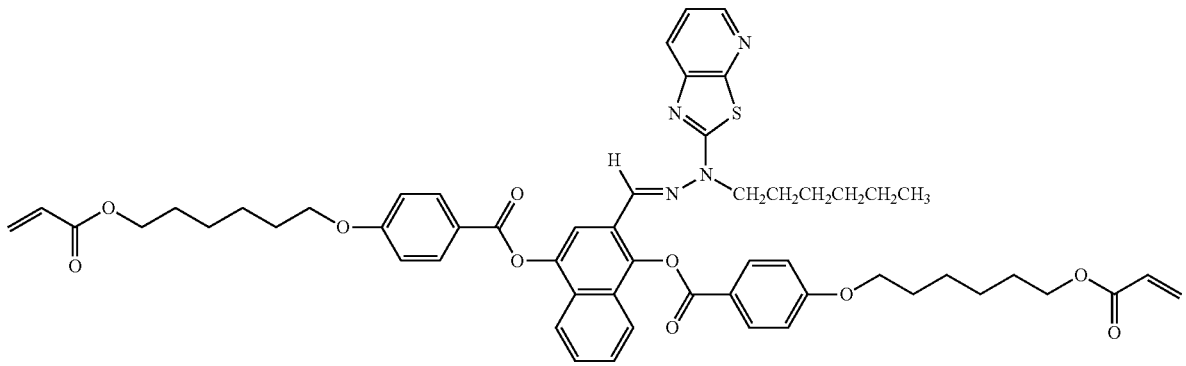

Compound 5

Step 1: Synthesis of Intermediate K

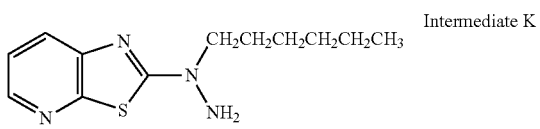

Intermediate K

A four-necked reactor equipped with a thermometer was charged with 1.32 g (7.95 mmol) of the intermediate B synthesized in the step 2 of Example 1 and 15 ml of DMF under a nitrogen stream to prepare a homogeneous solution. After the addition of 5.61 g (15.9 mmol) of cesium carbonate and 2.02 g (9.54 mmol) of 1-iodohexane to the solution, the mixture was stirred at 25° C. for 2 hours. After completion of the reaction, the reaction mixture was added to 200 ml of water, and extracted with 300 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a yellow solid. The yellow solid was purified by silica gel column chromatography (toluene:ethyl acetate=80:20) to obtain 738 mg of an intermediate K as a white solid (yield: 37.1%).

The structure of the target product was identified by $^1$H-NMR.

$^1$H-NMR (500 MHz, CDCl$_3$, TMS, δ ppm): 8.18 (dd, 1H, J=1.5 Hz, 4.5 Hz), 7.68 (dd, 1H, J=1.5 Hz, 8.3 Hz), 7.18 (dd, 1H, J=4.5 Hz, 8.3 Hz), 4.27 (s, 2H), 3.76 (t, 2H, J=7.5 Hz), 1.74 (tt, 2H, J=7.5 Hz, 7.5 Hz), 1.30-1.40 (m, 6H), 0.89 (t, 3H, J=7.0 Hz)

Step 2: Synthesis of Compound 5

A four-necked reactor equipped with a thermometer was charged with 738 mg (2.95 mmol) of the intermediate K synthesized in the step 1, 1.74 mg (2.35 mmol) of the intermediate I synthesized in Example 2, 3 ml of ethanol, and 20 ml of THF under a nitrogen stream to prepare a homogeneous solution. After the addition of 68.5 mg (0.30 mmol) of (±)-10-camphorsulfonic acid to the solution, the mixture was stirred at 40° C. for 3 hours. After completion of the reaction, the reaction mixture was added to 150 ml of water, and extracted with 300 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a white solid. The white solid was purified by silica gel column chromatography (toluene:ethyl acetate=90:10) to obtain 1.71 g of a compound 5 as a white solid (yield: 75.2%).

The structure of the target product was identified by $^1$H-NMR.

$^1$H-NMR (500 MHz, CDCl$_3$, TMS, δ ppm): 8.32 (d, 4H, J=9.0 Hz), 8.25 (dd, 1H, J=1.5 Hz, 4.5 Hz), 8.04 (s, 1H), 7.88-7.97 (m, 3H), 7.79 (dd, 1H, J=1.5 Hz, 8.0 Hz), 7.49-7.55 (m, 2H), 7.22 (dd, 1H, J=4.5 Hz, 8.0 Hz), 7.06 (d, 4H, J=9.0 Hz), 6.42 (dd, 2H, J=1.5 Hz, 17.5 Hz), 6.14 (dd, 2H, J=10.5 Hz, 17.5 Hz), 5.84 (dd, 2H, J=1.5 Hz, 10.5 Hz), 4.20 (t, 4H, J=6.5 Hz), 4.14-4.17 (m, 2H), 4.11 (t, 2H, J=6.5 Hz), 4.09 (t, 2H, J=6.5 Hz), 1.85-1.91 (m, 4H), 1.70-1.78 (m, 4H), 1.47-1.62 (m, 10H), 1.06-1.17 (m, 6H), 0.79 (t, 3H, J=6.5 Hz)

Example 6

Synthesis of Compound 6

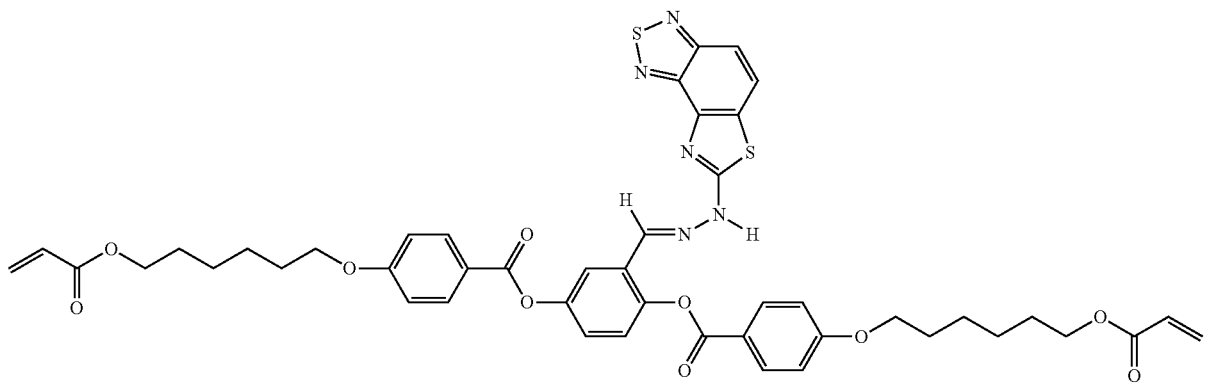

Compound 6

Step 1: Synthesis of Intermediate L

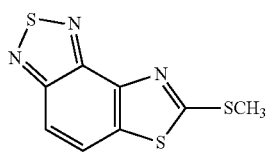

Intermediate L

A four-necked reactor equipped with a thermometer was charged with 1.50 g (8.08 mmol) of 4-amino-5-chloro-2,1,3-benzothiadiazole, 3.23 g (20.2 mmol) of potassium ethylxanthate, and 15 ml of DMF under a nitrogen stream to prepare a homogeneous solution. The solution was refluxed with heating for 18 hours, and the reaction mixture was cooled to 0° C. After the addition of 1.3 ml (21.0 mmol) of methyl iodide, the mixture was stirred at 0° C. for 1 hour. After completion of the reaction, the reaction mixture was added to 300 ml of water, and extracted with 500 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a yellow solid. The yellow solid was purified by silica gel column chromatography (toluene:ethyl acetate=90:10) to obtain 1.77 g of an intermediate L as a yellow solid (yield: 91.5%).

The structure of the target product was identified by $^{1}$H-NMR.

$^{1}$H-NMR (500 MHz, CDCl$_3$, TMS, δ ppm): 7.95 (d, 1H, J=9.0 Hz), 7.90 (d, 1H, J=9.0 Hz), 2.92 (s, 3H)

$^{13}$C-NMR (125 MHz, CDCl$_3$, TMS, δ ppm): 170.5, 154.8, 148.7, 144.4, 134.8, 122.5, 117.4, 16.4

Step 2: Synthesis of Intermediate M

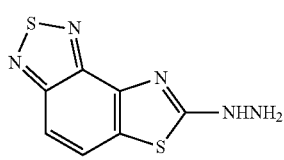

Intermediate M

A four-necked reactor equipped with a thermometer was charged with 1.00 g (4.18 mmol) of the intermediate L synthesized by the step 1, 1.0 ml (20.9 mmol) of hydrazine monohydrate, and 10 ml of 1-propanol under a nitrogen stream to prepare a homogenous solution. The solution was refluxed with heating for 8 hours. After completion of the reaction, the reaction mixture was cooled to 20° C., followed by addition of 20 ml of water to precipitate a solid, which was filtered off. The solid was washed with water, and dried using a vacuum dryer to obtain 640 mg of an intermediate M as a yellow solid (yield: 68.6%).

The structure of the target product was identified by $^{1}$H-NMR.

$^{1}$H-NMR (500 MHz, DMSO-d$_6$, TMS, δ ppm): 9.42 (s, 1H), 8.05 (d, 1H, J=9.0 Hz), 7.62 (d, 1H, J=9.0 Hz), 5.20 (s, 2H)

Step 3: Synthesis of Intermediate N

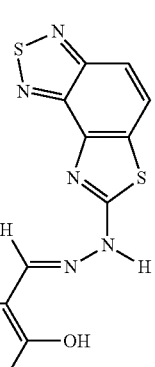

Intermediate N

A four-necked reactor equipped with a thermometer was charged with 394 mg (2.87 mmol) of 2,5-dihydroxybenzaldehyde, 640 mg (2.87 mmol) of the intermediate M synthesized by the step 2, and 10 ml of 1-propanol under a nitrogen stream to prepare a homogenous solution. The solution was refluxed with heating for 2 hours. After completion of the reaction, the reaction mixture was added to 100 ml of water to precipitate a solid, which was filtered off. The solid was washed with water, and dried using a vacuum dryer to obtain 923 mg of an intermediate N as a yellow solid (yield: 93.7%).

The structure of the target product was identified by $^1$H-NMR.

$^1$H-NMR (400 MHz, DMSO-d$_6$, TMS, δ ppm): 10.58 (brs, 1H), 9.38 (s, 1H), 8.93 (s, 1H), 8.35 (s, 1H), 8.17 (d, 1H, J=9.0 Hz), 7.76 (d, 1H, J=9.0 Hz), 7.12 (d, 1H, J=3.2 Hz), 6.71 (d, 1H, J=8.8 Hz), 6.66 (dd, 1H, J=3.2 Hz, 8.8 Hz)

Step 4: Synthesis of Compound 6

A four-necked reactor equipped with a thermometer was charged with 920 mg (2.68 mmol) of the intermediate N synthesized in the step 3, 1.80 g (6.16 mmol) of 4-(6-acryloylhex-1-yloxy)benzoic acid (manufactured by DKSH Japan K.K.), 164 mg (1.34 mmol) of 4-(dimethylamino)pyridine, and 25 ml of N-methylpyrrolidone under a nitrogen stream to prepare a homogeneous solution. After the addition of 1.34 g (6.97 mmol) of WSC to the solution, the mixture was stirred at 25° C. for 18 hours. After completion of the reaction, the reaction mixture was added to 300 ml of water, and extracted with 500 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a yellow solid. The yellow solid was purified by silica gel column chromatography (toluene:ethyl acetate=90:10) to obtain 1.21 g of a compound 6 as a yellow solid (yield: 50.6%).

The structure of the target product was identified by $^1$H-NMR.

$^1$H-NMR (500 MHz, DMSO-d$_6$, TMS, δ ppm): 12.78 (s, 1H), 8.23 (s, 1H), 8.17 (d, 2H, J=9.0 Hz), 8.14 (d, 2H, J=9.0 Hz), 8.10 (d, 1H, J=9.0 Hz), 7.785 (d, 1H, J=2.5 Hz), 7.784 (d, 1H, J=9.0 Hz), 7.47 (d, 1H, J=8.5 Hz), 7.43 (dd, 1H, J=2.5 Hz, 8.5 Hz), 7.18 (d, 2H, J=9.0 Hz), 7.15 (d, 2H, J=9.0 Hz), 6.33 (dd, 2H, J=1.5 Hz, 17.5 Hz), 6.19 (dd, 2H, J=10.5 Hz, 17.5 Hz), 5.95 (dd, 2H, J=1.5 Hz, 10.5 Hz), 4.10-4.14 (m, 8H), 1.75-1.81 (m, 4H), 1.63-1.69 (m, 4H), 1.39-1.51 (m, 8H)

Example 7

Synthesis of Compound 7

Step 1: Synthesis of Intermediate O

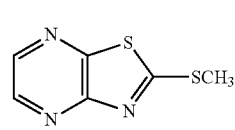

Intermediate O

A four-necked reactor equipped with a thermometer was charged with 3.46 g (26.7 mmol) of 2-amino-3-chloropyrazine, 8.56 g (53.4 mmol) of potassium ethylxanthate, and 30 ml of DMF under a nitrogen stream to prepare a homogeneous solution. The solution was refluxed with heating for 7 hours, and the reaction mixture was cooled to 0° C. After the addition of 3.3 ml (53.4 mmol) of methyl iodide, the mixture was stirred at 0° C. for 1 hour. After completion of the reaction, the reaction mixture was added to 300 ml of water, and extracted with 500 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a yellow solid. The yellow solid was purified by silica gel column chromatography (toluene:ethyl acetate=90:10) to obtain 4.38 g of an intermediate O as a light yellow solid (yield: 89.5%).

The structure of the target product was identified by $^1$H-NMR and $^{13}$C-NMR.

$^1$H-NMR (500 MHz, CDCl$_3$, TMS, δ ppm): 8.55 (d, 1H, J=2.5 Hz), 8.37 (d, 1H, J=2.5 Hz), 2.88 (s, 3H)

$^{13}$C-NMR (125 MHz, CDCl$_3$, TMS, δ ppm): 175.2, 158.0, 153.3, 141.7, 139.4, 15.4

Step 2: Synthesis of Intermediate P

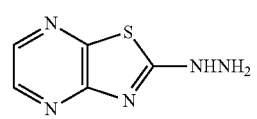

Intermediate P

A four-necked reactor equipped with a thermometer was charged with 1.50 g (8.19 mmol) of the intermediate O synthesized in the step 1, 4.0 ml (81.9 mmol) of hydrazine monohydrate, and 10 ml of ethanol under a nitrogen stream Compound 7

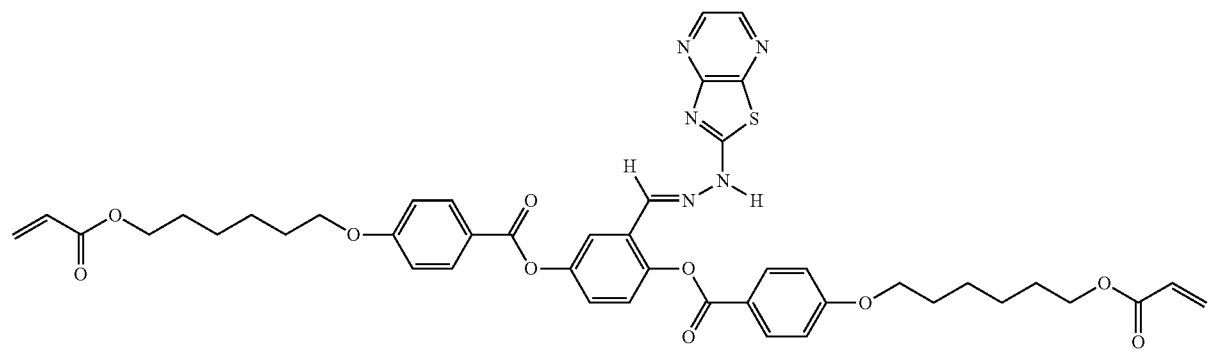

to prepare a homogenous solution. The solution was stirred at 25° C. for 5 hours. After completion of the reaction, the reaction mixture was added to 100 ml of water to precipitate a solid, which was filtered off. The solid was washed with water, and dried using a vacuum dryer to obtain 1.15 g of an intermediate P as a yellow solid (yield: 84.0%).

The structure of the target product was identified by $^1$H-NMR and $^{13}$C-NMR.

$^1$H-NMR (400 MHz, DMSO-$d_6$, TMS, δ ppm): 9.99 (brs, 1H), 8.17 (d, 1H, J=2.6 Hz), 7.97 (d, 1H, J=2.6 Hz), 5.30 (s, 2H)

$^{13}$C-NMR (100 MHz, DMSO-$d_6$, TMS, δ ppm): 175.5, 160.4, 150.8, 140.7, 135.3

Step 3: Synthesis of Compound 7

A four-necked reactor equipped with a thermometer was charged with 241 mg (1.44 mmol) of the intermediate P synthesized in the step 2, 940 mg (1.37 mmol) of the intermediate C synthesized in Example 1, 3 ml of ethanol, and 10 ml of THF under a nitrogen stream to prepare a homogeneous solution. After the addition of 33.4 mg (0.14 mmol) of (±)-10-camphorsulfonic acid to the solution, the mixture was stirred at 40° C. for 3 hours. After completion of the reaction, the reaction mixture was added to 150 ml of water, and extracted with 300 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a light yellow solid. The light yellow solid was purified by silica gel column chromatography (toluene:ethyl acetate=90:10) to obtain 1.01 g of a compound 7 as a light yellow solid (yield: 88.2%).

The structure of the target product was identified by $^1$H-NMR.

$^1$H-NMR (500 MHz, CDCl$_3$, TMS, δ ppm): 13.60 (brs, 1H), 8.96 (brs, 1H), 8.19 (d, 2H, J=9.0 Hz), 8.11 (d, 2H, J=8.5 Hz), 7.86 (d, 2H, J=2.5 Hz), 7.72 (d, 1H, J=2.5 Hz), 7.33 (dd, 1H, J=2.5 Hz, 8.5 Hz), 7.30 (d, 1H, J=8.5 Hz), 7.00 (d, 2H, J=9.0 Hz), 6.86 (d, 2H, J=8.5 Hz), 6.42 (dd, 1H, J=1.5 Hz, 17.5 Hz), 6.41 (dd, 1H, J=1.5 Hz, 17.5 Hz), 6.14 (dd, 1H, J=10.5 Hz, 17.5 Hz), 6.13 (dd, 1H, J=10.5 Hz, 17.5 Hz), 5.83 (dd, 1H, J=1.5 Hz, 10.5 Hz), 5.82 (dd, 1H, J=1.5 Hz, 10.5 Hz), 4.20 (t, 2H, J=6.5 Hz), 4.18 (t, 2H, J=6.5 Hz), 4.08 (t, 2H, J=6.0 Hz), 4.01 (t, 2H, J=6.5 Hz), 1.81-1.89 (m, 4H), 1.70-1.77 (m, 4H), 1.44-1.59 (m, 8H)

Example 8

Synthesis of Compound 8

Step 1: Synthesis of Intermediate Q

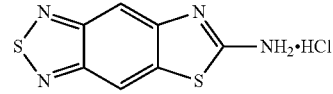

Intermediate Q

A three-necked reactor equipped with a thermometer was charged with 2.00 g (13.23 mmol) of 2,1,3-benzothiadiazole-5-amine and 60 ml of acetic acid under a nitrogen stream to prepare a homogeneous solution. The solution was cooled to 10° C. After the addition of 6.43 g (66.14 mmol) of potassium thiocyanate to the solution, 3.17 g (19.84 mmol) of bromine dissolved in 5 ml of acetic acid was added dropwise to the mixture over 15 minutes. After the dropwise addition, the mixture was stirred at 10° C. for 5 hours. After completion of the reaction, the reaction mixture was added to 700 ml of distilled water to precipitate a solid, which was filtered off. The resulting crystals were added to 100 ml of concentrated hydrochloric acid, and the mixture was stirred at 100° C. for 3 hours, and cooled to 25° C., followed by addition of 300 ml of distilled water. The precipitated crystals were filtered off, and dried using a vacuum dryer to obtain 2.01 g of an intermediate Q as a yellow solid (yield: 62%).

The structure of the target product was identified by $^1$H-NMR.

$^1$H-NMR (500 MHz, DMSO-$d_6$, TMS, δ ppm): 7.97 (s, 2H), 7.90 (d, 1H, J=9.5 Hz), 7.82 (d, 1H, J=9.5 Hz)

Step 2: Synthesis of Intermediate R

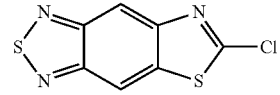

Intermediate R

A three-necked reactor equipped with a thermometer was charged with 1.80 g (7.36 mmol) of the intermediate Q and 60 ml of 6 N hydrochloric acid under a nitrogen stream to prepare a homogeneous solution. The solution was cooled to 0° C. After the addition of 5.08 g (73.55 mmol) of sodium nitrite over 30 minutes, the mixture was stirred at 0° C. for 1.5 hours. 3.64 g (36.78 mmol) of copper(I) chloride was added to the mixture over 15 minutes. After the addition, the mixture was stirred for 30 minutes. The reaction mixture was heated to 25° C., and stirred for 1 hour. The reaction

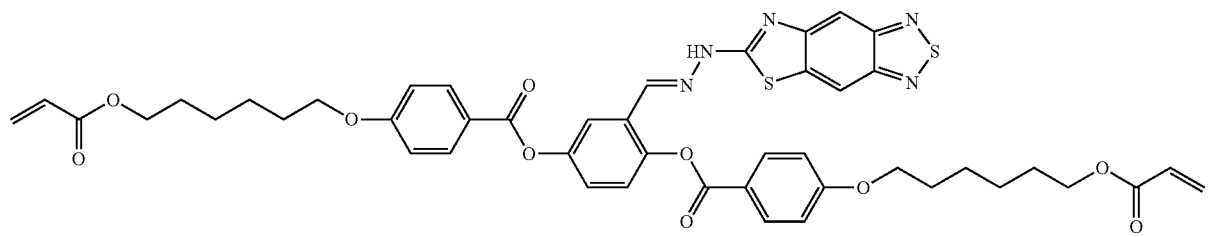

Compound 8 mixture was added 500 ml of distilled water to precipitate crystals. The crystals were filtered off, and dried using a vacuum dryer to obtain 1.29 g of an intermediate R as a light yellow solid (yield: 77%).

The structure of the target product was identified by $^1$H-NMR.

$^1$H-NMR (500 MHz, DMSO-d$_6$, TMS, δ ppm): 8.26 (d, 1H, J=9.5 Hz), 8.19 (d, 1H, J=9.5 Hz)

Step 3: Synthesis of Intermediate S

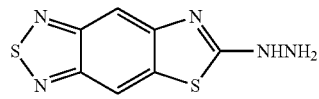

Intermediate S

A three-necked reactor equipped with a thermometer was charged with 0.70 g (3.07 mmol) of the intermediate R and 20 ml of ethanol under a nitrogen stream to prepare a homogeneous solution. After the addition of 1.15 g (23.06 mmol) of hydrazine monohydrate to the solution, the mixture was refluxed with heating for 1 hour. After completion of the reaction, 100 ml of distilled water was added to the reaction mixture to precipitate crystals. The crystals were filtered off, and dried using a vacuum dryer to obtain 0.68 g of an intermediate S as a yellow solid (yield: 90%).

The structure of the target product was identified by $^1$H-NMR.

$^1$H-NMR (500 MHz, DMSO-d$_6$, TMS, δ ppm): 9.51 (s, 1H), 7.88 (d, 1H, J=9.5 Hz), 7.79 (d, 1H, J=9.5 Hz), 5.29 (s, 2H)

Step 4: Synthesis of Compound 8

A three-necked reactor equipped with a thermometer was charged with 2.00 g (2.32 mmol) of the intermediate C and 20 ml of THF under a nitrogen stream to prepare a homogeneous solution. After the addition of 0.58 ml (0.58 mmol) of 1 N hydrochloric acid to the solution, 0.68 g (3.06 mmol) of the intermediate S was added to the mixture over 30 minutes, and the mixture was stirred at 25° C. for 1 hour. The reaction mixture was concentrated using a rotary evaporator, and the concentrate was purified by silica gel column chromatography (chloroform:THF=97:3) to obtain 1.70 g of a compound 8 as a yellow solid (yield: 65%).

The structure of the target product was identified by $^1$H-NMR.

$^1$H-NMR (500 MHz, DMSO-d$_6$, TMS, δ ppm): 12.76 (s, 1H), 8.24 (s, 1H), 8.17 (d, 2H, J=9.0 Hz), 8.14 (d, 2H, J=9.0 Hz), 7.95 (d, 1H, J=9.0 Hz), 7.91 (d, 1H, J=9.0 Hz), 7.83 (d, 1H, J=2.5 Hz), 7.41-7.49 (m, 2H), 7.17 (d, 2H, J=9.0 Hz), 7.15 (d, 2H, J=9.0 Hz), 6.33 (dd, 2H, J=1.5 Hz, 17.5 Hz), 6.19 (dd, 2H, J=10.5 Hz, 17.5 Hz), 5.94 (dd, 2H, J=1.5 Hz, 10.5 Hz), 4.08-4.16 (m, 8H), 1.73-1.83 (m, 4H), 1.60-1.71 (m, 4H), 1.35-1.53 (m, 8H)

Synthesis Example 1

Synthesis of Compound A

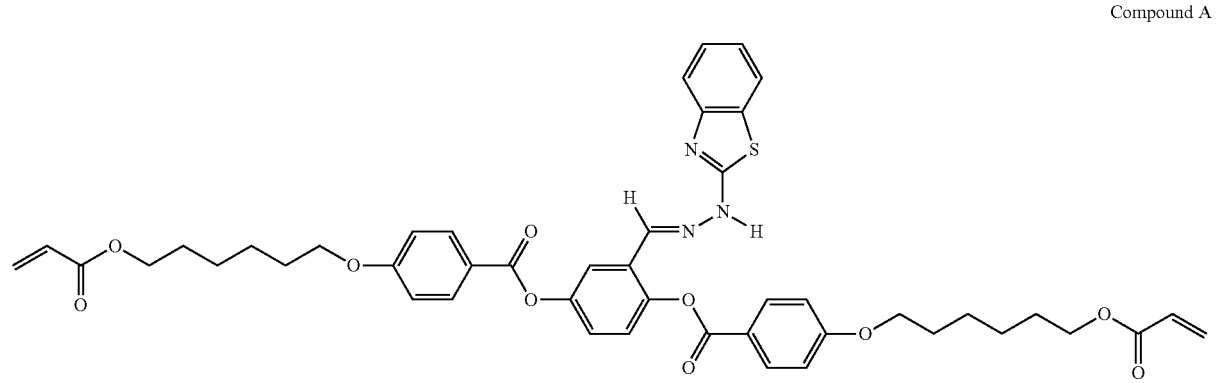 [SMILES: C=CC(=O)OCCCCCCOc1ccc(C(=O)Oc2ccc(OC(=O)c3ccc(OCCCCCCOC(=O)C=C)cc3)c(/C=N/Nc3nc4ccccc4s3)c2)cc1]

Compound A

A four-necked reactor equipped with a thermometer was charged with 10.5 g (15.3 mmol) of the intermediate C synthesized in the step 3 of Example 1, 3.0 g (18.3 mmol) of 2-hydrazinobenzothiazole, and 80 ml of THF under a nitrogen stream to prepare a homogeneous solution. After the addition of 18 mg (0.08 mmol) of (±)-10-camphorsulfonic acid to the solution, the mixture was stirred at 25° C. for 3 hours. After completion of the reaction, the reaction mixture was added to 800 ml of 10% sodium bicarbonate water, and extracted twice with 100 ml of ethyl acetate. The ethyl acetate layer was collected, and dried over anhydrous sodium sulfate, and sodium sulfate was removed by filtration. Ethyl acetate was evaporated from the filtrate under reduced pressure using a rotary evaporator to obtain a light yellow solid. The light yellow solid was purified by silica gel column chromatography (toluene:ethyl acetate=8:2) to obtain 8.0 g of a compound A as a light yellow solid (yield: 62.7%).

The structure of the target product was identified by $^1$H-NMR and mass spectroscopy.

$^1$H-NMR (500 MHz, DMSO-d$_6$, TMS, δ ppm): 12.30 (br, 1H), 8.19 (s, 1H), 8.17-8.12 (m, 4H), 7.76 (d, 1H, J=3.0 Hz), 7.68 (d, 1H, J=7.5 Hz), 7.45-7.39 (m, 3H), 7.28 (t, 1H, J=8.0 Hz), 7.18-7.14 (m, 4H), 7.09 (t, 1H, J=8.0 Hz), 6.33 (dd, 2H, J=1.5 Hz, 17.5 Hz), 6.18 (dd, 2H, J=10.5 Hz, 17.5 Hz), 5.944 (dd, 1H, J=1.5 Hz, 10.5 Hz), 5.941 (dd, 1H, J=1.5 Hz, 10.5 Hz), 4.14-4.10 (m, 8H), 1.80-1.75 (m, 4H), 1.69-1.63 (m, 4H), 1.53-1.38 (m, 8H)

LCMS (APCI): calcd for $C_{46}H_{47}N_3O_{10}S$: 833 [M+]. Found: 833.

The phase transition temperature was measured by the following method using the compounds 1 to 8 obtained in Examples 1 to 8, the compound A obtained in Synthesis Example 1, the compound 1r of Reference Example 1 ("K35" manufactured by Zeon Corporation) (see below), and the compound 2r of Reference Example 2 ("LC242" manufactured by BASF) (see below).

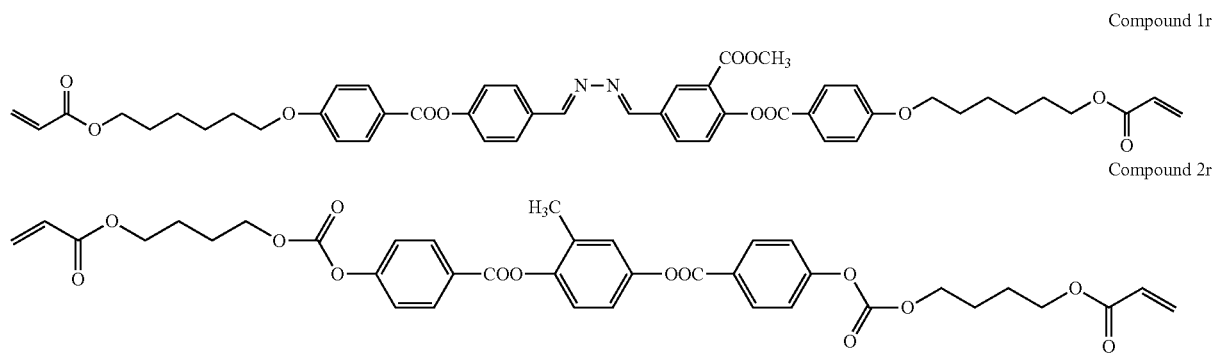

Compound 1r

Compound 2r

Measurement of Phase Transition Temperature 10 mg of each compound (compounds 1 to 8, A, 1r, and 2r) was weighed, and placed in a solid state between two glass substrates provided with a polyimide alignment film subjected to a rubbing treatment (manufactured by E.H.C. Co. Ltd.). The substrates were placed on a hot plate, heated from 40° C. to 200° C., and cooled to 40° C. A change in structure when the temperature was changed was observed using a polarizing microscope ("ECLIPSE LV 100 POL" manufactured by Nikon Corporation). Note that the phase transition temperature of the compound 7 was measured within the range of 40° C. to 250° C.

The phase transition temperature measurement results are shown in Table 1. In Table 1, "C" refers to "Crystal", "N" refers to "Nematic", "I" refers to "Isotropic", and "SmA" refers to "Smectic A". The term "Crystal" means that the test compound was in a solid phase, the term "Nematic" means that the test compound was in a nematic liquid crystal phase, the term "Isotropic" means that the test compound was in an isotropic liquid phase, and the term "Smectic A" means that the test compound was in a smectic A phase.

TABLE 1

| | Compound No. | Phase transition temperature |
|---|---|---|
| Example 1 | Compound 1 | C ⇌(40° C. or less) N(169° C.)⇌(166° C.) I(180° C.) |
| Example 2 | Compound 2 | C ⇌(40° C. or less) N(192° C.)⇌(137° C.) I |
| Example 3 | Compound 3 | C ⇌(40° C. or less) N(197° C.)⇌(140° C.) I |
| Example 4 | Compound 4 | C ⇌(40° C. or less) N(135° C.)⇌(67° C.) SmA ⇌(80° C.) I |
| Example 5 | Compound 5 | C ⇌(40° C. or less) N(140° C.)⇌(53° C.) I |
| Example 6 | Compound 6 | C ⇌(40° C. or less) N(165° C.)⇌(188° C.) I(195° C.) |
| Example 7 | Compound 7 | C ⇌(145° C.) I(230° C.) |
| Example 8 | Compound 8 | C ⇌(40° C. or less) N(182° C.)⇌(175° C.) I(188° C.) |
| Synthesis Example 1 | Compound A | C ⇌(50° C. or less) N(102° C.)⇌(140° C.) I(165° C.) |
| Reference Example 1 | Compound 1r | C ⇌(40° C. or less) N(80° C.) I(200° C. or more) |
| Reference Example 2 | Compound 2r | C ⇌(40° C. or less) N(60° C.)⇌(122° C.) I(123° C.) |

Example 9

1.0 g of the compound 1 obtained in Example 1, 30 mg of a photoinitiator A ("Adekaoptomer N-1919" manufactured by Adeka Corporation (hereinafter the same)), and 100 mg of a 1% cyclopentanone solution of a surfactant A ("KH-40"

manufactured by AGC Seimi Chemical Co., Ltd.) were dissolved in 2.3 g of dimethyl sulfoxide. The solution was filtered through a disposable filter having a pore size of 0.45 µm to obtain a polymerizable composition 1.

Example 10

0.5 g of the compound 1 obtained in Example 1, 0.5 g of the compound A obtained in Synthesis Example 1, 30 mg of the photoinitiator A, and 100 mg of a 1% cyclopentanone solution of the surfactant A were dissolved in 4.0 g of cyclopentanone. The solution was filtered through a disposable filter having a pore size of 0.45 µm to obtain a polymerizable composition 2.

Example 11

1.0 g of the compound 2 obtained in Example 2, 30 mg of the photoinitiator A, and 100 mg of a 1% cyclopentanone solution of the surfactant A were dissolved in 5.7 g of dimethyl sulfoxide. The solution was filtered through a disposable filter having a pore size of 0.45 µm to obtain a polymerizable composition 3.

Example 12

0.5 g of the compound 2 obtained in Example 2, 0.5 g of the compound A obtained in Synthesis Example 1, 30 mg of the photoinitiator A, and 100 mg of a 1% cyclopentanone solution of the surfactant A were dissolved in 4.0 g of cyclopentanone. The solution was filtered through a disposable filter having a pore size of 0.45 µm to obtain a polymerizable composition 4.

Example 13

0.67 g of the compound 3 obtained in Example 3, 0.33 g of the compound A obtained in Synthesis Example 1, 30 mg of the photoinitiator A, and 100 mg of a 1% cyclopentanone solution of the surfactant A were dissolved in 5.7 g of dimethyl sulfoxide. The solution was filtered through a disposable filter having a pore size of 0.45 µm to obtain a polymerizable composition 5.

Example 14

0.5 g of the compound 3 obtained in Example 3, 0.5 g of the compound A obtained in Synthesis Example 1, 30 mg of the photoinitiator A, and 100 mg of a 1% cyclopentanone solution of the surfactant A were dissolved in 1.65 g of dimethyl sulfoxide and 2.35 g of cyclopentanone. The solution was filtered through a disposable filter having a pore size of 0.45 µm to obtain a polymerizable composition 6.

Example 15

0.5 g of the compound 4 obtained in Example 4, 0.5 g of the compound A obtained in Synthesis Example 1, 30 mg of the photoinitiator A, and 100 mg of a 1% cyclopentanone solution of the surfactant A were dissolved in 4.0 g of cyclopentanone. The solution was filtered through a disposable filter having a pore size of 0.45 µm to obtain a polymerizable composition 7.

Example 16

0.67 g of the compound 5 obtained in Example 5, 0.33 g of the compound A obtained in Synthesis Example 1, 30 mg of the photoinitiator A, and 100 mg of a 1% cyclopentanone solution of the surfactant A were dissolved in 2.3 g of cyclopentanone. The solution was filtered through a disposable filter having a pore size of 0.45 µm to obtain a polymerizable composition 8.

Example 17

1.0 g of the compound 6 obtained in Example 6, 30 mg of the photoinitiator A, and 100 mg of a 1% cyclopentanone solution of the surfactant A were dissolved in 2.4 g of cyclopentanone. The solution was filtered through a disposable filter having a pore size of 0.45 µm to obtain a polymerizable composition 9.

Example 18

0.2 g of the compound 7 obtained in Example 7, 0.8 g of the compound A obtained in Synthesis Example 1, 30 mg of the photoinitiator A, and 100 mg of a 1% cyclopentanone solution of the surfactant A were dissolved in 0.94 g of cyclopentanone and 4.2 g of chloroform. The solution was filtered through a disposable filter having a pore size of 0.45 µm to obtain a polymerizable composition 10.

Example 19

1.0 g of the compound 8 obtained in Example 8, 30 mg of the photoinitiator A, and 100 mg of a 1% cyclopentanone solution of the surfactant A were dissolved in 2.3 g of cyclopentanone and 0.7 g of dimethyl sulfoxide. The solution was filtered through a disposable filter having a pore size of 0.45 µm to obtain a polymerizable composition 11.

Example 20

0.5 g of the compound 8 obtained in Example 8, 0.5 g of the compound A obtained in Synthesis Example 1, 30 mg of the photoinitiator A, and 100 mg of a 1% cyclopentanone solution of the surfactant A were dissolved in 2.3 g of cyclopentanone. The solution was filtered through a disposable filter having a pore size of 0.45 µm to obtain a polymerizable composition 12.

Example 21

0.5 g of the compound 8 obtained in Example 8, 0.5 g of the compound 5 obtained in Example 12, 30 mg of the photoinitiator A, and 100 mg of a 1% cyclopentanone solution of the surfactant A were dissolved in 2.3 g of cyclopentanone. The solution was filtered through a disposable filter having a pore size of 0.45 µm to obtain a polymerizable composition 13.

Comparative Examples 1 and 2

1.0 g of the compound 1r or 2r, 30 mg of the photoinitiator A, and 100 mg of a 1% cyclopentanone solution of the surfactant A were dissolved in 2.3 g of cyclopentanone. The solution was filtered through a disposable filter having a pore size of 0.45 µm to obtain a polymerizable composition 1r or 2r, respectively.

Measurement of Retardation and Evaluation of Wavelength Dispersion (i) Formation of Liquid Crystal Layer Using Polymerizable Composition Each polymerizable composition (polymerizable compositions 1 to 13, 1r, and 2r) was applied to a transparent glass substrate provided with a polyimide alignment film subjected to a rubbing treatment (manufactured by E.H.C. Co. Ltd.) using a #6 wire bar. The resulting film was dried for 30 seconds at the temperature shown in Table 2, and subjected to an alignment treatment for 1 minute at the temperature shown in Table 2 to form a liquid crystal layer. UV rays were applied to the liquid crystal layer at a dose of 2000 mJ/cm² to effect polymerization to prepare a wavelength dispersion measurement sample.

(ii) Measurement of Retardation

The retardation between 400 nm and 800 nm was measured using the sample utilizing an ellipsometer ("M2000U" manufactured by J. A. Woollam).

(iii) Evaluation of Wavelength Dispersion

The wavelength dispersion was evaluated from the values $\alpha$ and $\beta$ calculated by the following expressions using the measured retardation.

$\alpha$=(retardation at 449.9 nm)/(retardation at 548.5 nm)

$\beta$=(retardation at 650.2 nm)/(retardation at 548.5 nm)

The value $\alpha$ is smaller than 1, and the value $\beta$ is larger than 1 when ideal wideband wavelength dispersion (reverse wavelength dispersion) is achieved. The values $\alpha$ and $\beta$ are almost identical when flat wavelength dispersion is achieved. The value $\alpha$ is larger than 1, and the value $\beta$ is smaller than 1 when normal dispersion is achieved.

Flat wavelength dispersion that ensures that the values $\alpha$ and $\beta$ are almost identical is preferable, and reverse wavelength dispersion that ensures that the value $\alpha$ is smaller than 1, and the value $\beta$ is larger than 1, is particularly preferable.

Table 2 shows the thickness (μm) of the liquid crystal polymer films obtained by polymerizing the polymerizable compositions, the retardation (Re) at a wavelength of 548.5 nm, and the values $\alpha$ and $\beta$.

Note that "Ratio (%)" in Table 2 refers to the ratio (mass %) with respect to the total amount of the polymerizable compounds 1 and 2.

TABLE 2

| | Polymerizable composition | Polymerizable compound 1 | | Polymerizable compound 2 | | Drying temperature (° C.) | Alignment treatment temperature (° C.) | Thickness (μm) | Re (548.5 nm) | $\alpha$ | $\beta$ |
|---|---|---|---|---|---|---|---|---|---|---|---|
| | | Type | Ratio (%) | Type | Ratio (%) | | | | | | |
| Example 9 | 1 | Compound 1 | 100 | — | — | 185 | 23 | 3.291 | 140.54 | 0.786 | 1.038 |
| Example 10 | 2 | Compound 1 | 50 | Compound A | 50 | 110 | 23 | 1.870 | 89.32 | 0.839 | 1.023 |
| Example 11 | 3 | Compound 2 | 100 | — | — | 195 | 23 | 1.000 | 64.85 | 0.392 | 1.085 |
| Example 12 | 4 | Compound 2 | 50 | Compound A | 50 | 110 | 23 | 1.812 | 121.14 | 0.677 | 1.045 |
| Example 13 | 5 | Compound 3 | 67 | Compound A | 33 | 200 | 23 | 1.511 | 65.07 | 0.626 | 1.052 |
| Example 14 | 6 | Compound 3 | 50 | Compound A | 50 | 200 | 23 | 1.811 | 91.64 | 0.727 | 1.044 |
| Example 15 | 7 | Compound 4 | 50 | Compound A | 50 | 110 | 23 | 1.532 | 105.04 | 0.815 | 1.060 |
| Example 16 | 8 | Compound 5 | 67 | Compound A | 33 | 150 | 25 | 1.451 | 79.31 | 0.760 | 1.027 |
| Example 17 | 9 | Compound 6 | 100 | — | — | 170 | 25 | 1.287 | 94.82 | 0.458 | 1.078 |
| Example 18 | 10 | Compound 7 | 20 | Compound A | 80 | 150 | 25 | 2.151 | 182.99 | 0.870 | 1.016 |
| Example 19 | 11 | Compound 8 | 100 | — | — | 200 | 25 | 1.259 | 92.40 | 0.952 | 1.000 |
| Example 20 | 12 | Compound 8 | 50 | Compound A | 50 | 120 | 25 | 1.854 | 130.76 | 0.940 | 1.006 |
| Example 21 | 13 | Compound 8 | 50 | Compound 5 | 50 | 150 | 25 | 1.800 | 121.29 | 0.887 | 1.019 |
| Comparative Example 1 | 1r | Compound 1r | 100 | — | — | 90 | 23 | 1.509 | 355.97 | 1.193 | 0.918 |
| Comparative Example 2 | 2r | Compound 2r | 100 | — | — | 80 | 23 | 1.479 | 222.9 | 1.086 | 0.970 |

As shown in Table 2, the optically anisotropic articles obtained using the polymerizable compositions 1 to 13 obtained in Examples 9 to 21 had reverse wavelength dispersion in which the value $\alpha$ was smaller than 1, and the value $\beta$ was larger than 1. On the other hand, the optically anisotropic articles obtained using the polymerizable compositions 1r and 2r obtained in Comparative Examples 1 and 2 had normal dispersion in which the value $\alpha$ was larger than 1, and the value $\beta$ was smaller than 1.

The invention claimed is:

1. A polymerizable compound represented by a formula (I),

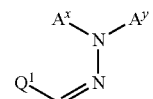

(I)

wherein Y$^1$ to Y$^6$ are independently a chemical single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$—, or —NR$^1$—O—, R$^1$ is a hydrogen atom or an alkyl group having 1 to 6 carbon atoms, G$^1$ and G$^2$ are independently a substituted or unsubstituted divalent aliphatic group having 1 to 20 carbon atoms that optionally includes —O—, —S—, —C(=O)—O—, —O—C(=O)—O—, —NR$^2$—C(=O)—, —C(=O)—NR$^2$—, —NR$^2$—, or —C(=O)—, provided that a case where the aliphatic group includes two or more adjacent —O— or —S— is excluded, R$^2$ is a hydrogen atom or an alkyl group having 1 to 6 carbon atoms, Z$^1$ and Z$^2$ are independently an alkenyl group having 2 to 10 carbon atoms that is unsubstituted, or substituted with a halogen atom, A$^x$ is a fused ring group represented by a formula (II),

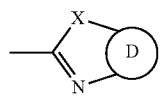
(II)

wherein X is —NR$^3$—, an oxygen atom, a sulfur atom, —C(=O)—, —SO—, or —SO$_2$—, R$^3$ is a hydrogen atom or an alkyl group having 1 to 6 carbon atoms, and D is a substituted or unsubstituted ring having 1 to 20 carbon atoms that includes at least one nitrogen atom, A$^y$ is a hydrogen atom, a substituted or unsubstituted alkyl group having 1 to 20 carbon atoms, a substituted or unsubstituted alkenyl group having 2 to 20 carbon atoms, a substituted or unsubstituted cycloalkyl group having 3 to 18 carbon atoms, —C(=O)—R$^4$, —SO$_2$—R$^5$, or an organic group having 2 to 30 carbon atoms that includes at least one aromatic ring selected from a group consisting of an aromatic hydrocarbon ring and an aromatic heterocyclic ring, provided that the aromatic ring is either substituted or unsubstituted, R$^4$ is a substituted or unsubstituted alkyl group having 1 to 20 carbon atoms, a substituted or unsubstituted alkenyl group having 2 to 20 carbon atoms, or a substituted or unsubstituted cycloalkyl group having 3 to 18 carbon atoms, R$^5$ is an alkyl group having 1 to 20 carbon atoms, an alkenyl group having 2 to 20 carbon atoms, a phenyl group, or a 4-methylphenyl group, A$^1$ is a substituted or unsubstituted trivalent aromatic group, A$^2$ and A$^3$ are independently a substituted or unsubstituted divalent aromatic group having 6 to 30 carbon atoms, and Q$^1$ is a hydrogen atom, or a substituted or unsubstituted alkyl group having 1 to 6 carbon atoms.

2. The polymerizable compound according to claim 1, wherein A$^x$ is a fused ring group represented by a formula (II-1), a fused ring group represented by a formula (II-2), a fused ring group represented by a formula (II-3), a fused ring group represented by a formula (II-4), or a fused ring group represented by a formula (II-5),

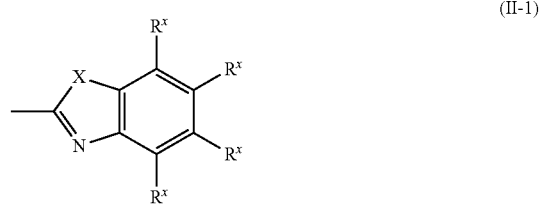
(II-1)

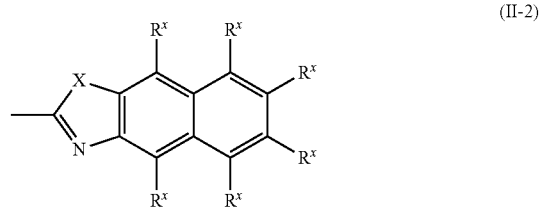
(II-2)

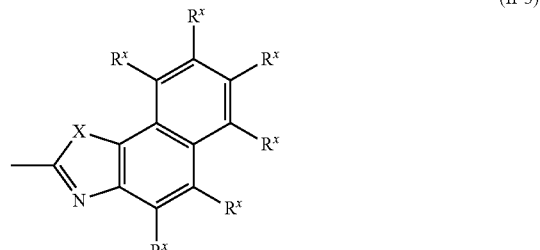
(II-3)

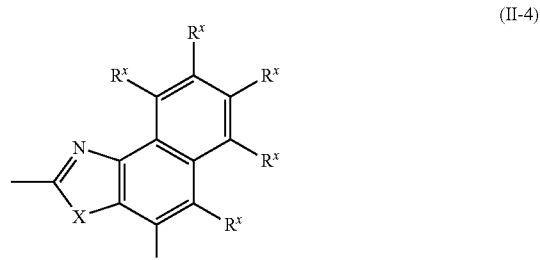
(II-4)

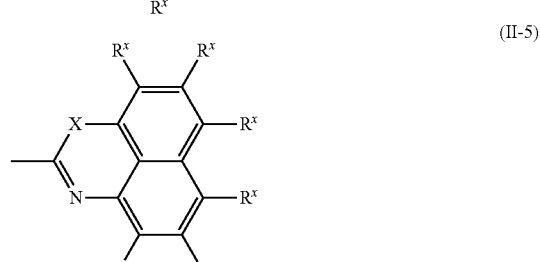
(II-5)

wherein X is the same as defined above, at least one C—R$^x$ in each formula is substituted with a nitrogen atom, R$^x$ are a hydrogen atom, a halogen atom, an alkyl group having 1 to 6 carbon atoms, a cyano group, a nitro group, an alkylsulfinyl group having 1 to 6 carbon atoms, an alkylsulfonyl group having 1 to 6 carbon atoms, a fluoroalkyl group having 1 to 6 carbon atoms, an alkoxy group having 1 to 6 carbon atoms, an alkylthio group having 1 to 6 carbon atoms, a monosubstituted amino group, a disubstituted amino group, an alkylsulfamoyl group having 1 to 6 carbon atoms, a dialkylsulfamoyl group having 2 to 12 carbon atoms, or —C(=O)—O—R$^6$, and R$^6$ is a hydrogen atom or an alkyl group having 1 to 6 carbon atoms, provided that R$^x$ are either identical or different, and adjacent C—R$^x$ optionally form a ring.

3. The polymerizable compound according to claim 1, wherein A$^1$ is a substituted or unsubstituted trivalent benzene ring group, or a substituted or unsubstituted trivalent naphthalene ring group, and $A^2$ and $A^3$ are independently a substituted or unsubstituted phenylene group, or a substituted or unsubstituted naphthylene group.

4. The polymerizable compound according to claim 1, wherein $Y^1$ to $Y^6$ are independently a chemical single bond, —O—, —O—C(=O)—, —C(=O)—O—, or —O—C(=O)—O—.

5. The polymerizable compound according to claim 1, wherein $Z^1$ and $Z^2$ are independently $CH_2$=CH—, $CH_2$=C($CH_3$)—, or $CH_2$=C(Cl)—.

6. The polymerizable compound according to claim 1, wherein $G^1$ and $G^2$ are independently a substituted or unsubstituted divalent aliphatic group having 1 to 12 carbon atoms that optionally includes —O—, —O—C(=O)—, —C(=O)—O—, or —C(=O)—, provided that a case where the aliphatic group includes two or more adjacent —O— is excluded.

7. The polymerizable compound according to claim 1, wherein $G^1$ and $G^2$ are independently a divalent alkylene group having 1 to 12 carbon atoms.

8. A polymerizable composition comprising at least one polymerizable compound according to claim 1.

9. A polymerizable composition comprising the polymerizable compound according to claim 1, and an initiator.

10. A polymer obtained by polymerizing the polymerizable compound according to claim 1.

11. The polymer according to claim 10, the polymer being a liquid crystalline polymer.

12. An optically anisotropic article comprising the polymer according to claim 11.

13. The polymerizable compound according to claim 1, wherein the total number of atoms in the ring D is 4 to 25.

* * * * *